United States Patent
Wang et al.

(10) Patent No.: US 10,858,396 B2
(45) Date of Patent: *Dec. 8, 2020

(54) HER2 PEPTIDE REGENTS AND METHODS

(71) Applicant: THE REGENTS OF THE UNIVERSITY OF MICHIGAN, Ann Arbor, MI (US)

(72) Inventors: Thomas D. Wang, Ann Arbor, MI (US); Bishnu P. Joshi, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 28 days.

This patent is subject to a terminal disclaimer.

(21) Appl. No.: 15/780,286

(22) PCT Filed: Dec. 1, 2016

(86) PCT No.: PCT/US2016/064410
§ 371 (c)(1),
(2) Date: May 31, 2018

(87) PCT Pub. No.: WO2017/096036
PCT Pub. Date: Jun. 8, 2017

(65) Prior Publication Data
US 2018/0273584 A1    Sep. 27, 2018

Related U.S. Application Data

(60) Provisional application No. 62/262,159, filed on Dec. 2, 2015.

(51) Int. Cl.
*A61K 38/00* (2006.01)
*C07K 7/06* (2006.01)
*A61K 49/00* (2006.01)
*C07K 7/00* (2006.01)
*C07K 14/00* (2006.01)
*A61K 47/64* (2017.01)
*G01N 33/574* (2006.01)

(52) U.S. Cl.
CPC ............... *C07K 7/06* (2013.01); *A61K 38/00* (2013.01); *A61K 47/64* (2017.08); *A61K 49/0056* (2013.01); *C07K 7/00* (2013.01); *C07K 14/00* (2013.01); *G01N 33/57492* (2013.01); *G01N 2333/485* (2013.01); *G01N 2333/705* (2013.01); *G01N 2333/82* (2013.01); *G01N 2800/52* (2013.01)

(58) Field of Classification Search
CPC ........ A61K 47/00; A61K 47/64; A61K 38/00; A61K 49/00; A61K 49/0056; C07K 7/06; C07K 14/00; C07K 7/00; G01N 33/57492; G01N 2800/52; G01N 2333/82; G01N 2333/705; G01N 2333/485

USPC .......... 424/1.11, 1.65, 1.69, 1.81, 1.85, 1.89, 424/9.1, 9.2, 9.3, 9.4, 9.5, 9.6; 514/1, 514/1.1, 19.2, 19.3, 19.4, 19.5, 19.6, 21.7, 514/21.8; 530/300, 329
See application file for complete search history.

(56) References Cited

U.S. PATENT DOCUMENTS

2006/0276379 A1    12/2006    Krag et al.

OTHER PUBLICATIONS

Baselga et al., "Novel anticancer targets: revisiting ERBB2 and discovering ERBB3," Nature Reviews Cancer, 9: 463-475 (2009).
Brandt-Rauf et al., "The c-erbB-2 protein in oncogenesis: molecular structure to molecular epidemiology," Critical Reviews in Oncogenesis, 5:313-329 (1994).
Cwirla et al., "Peptides on phage: A vast library of peptides for identifying ligands," Proc. Natl. Acad. Sci. USA, 87:6378-6382 (1990).
Fornaro et al., "Anti-HER agents in gastric cancer: from bench to bedside," Nature Reviews Gastroenterology and Hepatology, 8(7):369-383 (2011).
Franklin et al., "Insights into ErbB signaling from the structure of the ErbB2-pertuzumab complex," Cancer Cell, 5:317-328 (2009).
Garrett et al., "The Crystal Structure of a Truncated ErbB2 Ectodomain Reveals an Active Conformation, Poised to Interact with Other ErbB Receptors," Mol Cell. 11:495-505 (2003).
Geng et al., "Structure-based Design of Peptides with High Affinity and Specificity to HER2 Positive Tumors," Theranostics 5(10):1154-1165 (2015).
International Preliminary Report on Patentability from International Application No. PCT/US2016/064410 dated Jun. 5, 2018.
International Search Report and Written Opinion from International Application No. PCT/US2016/064410 dated Apr. 10, 2017.
Joshi et al., "Design and Synthesis of Near-Infrared Peptide for in Vivo Molecular Imaging of HER2," Bioconjug Chem 27(2):481-494 (2016).
Katz et al., "Regulation of MAPKs by growth factors and receptor tyrosine kinases," Biochim Biophys Acta. 1773(8) 1161-1176 (2007).
Kelly et al., "Detection of Invasive Colon Cancer Using a Novel, Targeted, Library-Derived Fluorescent Peptide," Cancer Res, 64:6247-51 (2004).

(Continued)

*Primary Examiner* — D. L. Jones
(74) *Attorney, Agent, or Firm* — Marshall, Gerstein & Borun LLP

(57) ABSTRACT

The present disclosure is directed to HER2-specific peptide reagents, methods for detecting pre-cancer (dysplasia), early cancer and/or cancer using the peptide reagents, and methods for targeting pre-cancerous (dysplastic) cells, and/or cancer cells using the peptide reagents.

20 Claims, 23 Drawing Sheets
Specification includes a Sequence Listing.

(56) References Cited

OTHER PUBLICATIONS

Khelwatty et al., "Co-Expression of HER FAmily Members in Patients with Dukes' C and D Colon Cancer and Their Impacts on Patient Prognosis and Survival," PLoS ONE, 9(3):e91139 (2014).
Larimer et al., "Affinity Maturation of an ERBB2-Targeted SPECT Imaging Peptide by In Vivo Phage Display," Mol Imaging Biol 16:449-458 (2014).
Lemmon, "Ligand-induced ErbB receptor dimerization," Exp. Cell Res., 315:638-648 (2009).
Mitri et al., "The HER2 Receptor in Breast Cancer: Pathophysiology, Clinical Use, and New Advances in Therapy," Chemother Res Pract, 743:193 (2012).
Pasqualini et al., "Organ targeting in vivo using phage display peptide libraries," Nature 380:364-366 (1996).
Ross et al., "The HER-2/neu Oncogene in Tumors of the Gastrointestinal Tract," Cancer Invest. 19(5):554-68 (2001).
Scott et al., "Searching for Peptide Ligands with an Epitope Library," Science 249:386-390 (1990).
Seo et al., "HER2 Status in Colorectal Cancer: Its Clinical Significance and the Relationship between HER2 Gene Amplification and Expression," PLoS ONE, 9(5):e98528 (2014).
Shaib et al., "The Epidemiology of Cholangiocarcinoma," Semin Liver Dis, 24: 115-125 (2004).
Tao et al., "All EGF(ErbB) receptors have performed homo- and heterodimeric structures in living cells," Journal of Cell Science, 121:3207-3217 (2008).
Trabuco et al., "PepSite: prediction of peptide-binding sites from protein surfaces," Nucleic Acids Res., 40:W423-427 (2012).
UniProtKB/TrEMBL Submission U1QBL7_9ACTO, (Jun. 24, 2015) Retrieved from the Internet Jan. 20, 2017): <www.uniprot.org/uniprot/U1QBL7.txt?version=6>]; amino acids 158-164, 100% identity to SEQ ID No. 1.
Vogelstein et al., "Cancer Genome Landscapes," Science 339:1546-1558 (2013).
Wang et al., "Microarray Based Screening of Peptide Nano Probes for HER2 Positive Tumor," Anal Chem. 18:8367-8372 (2015).

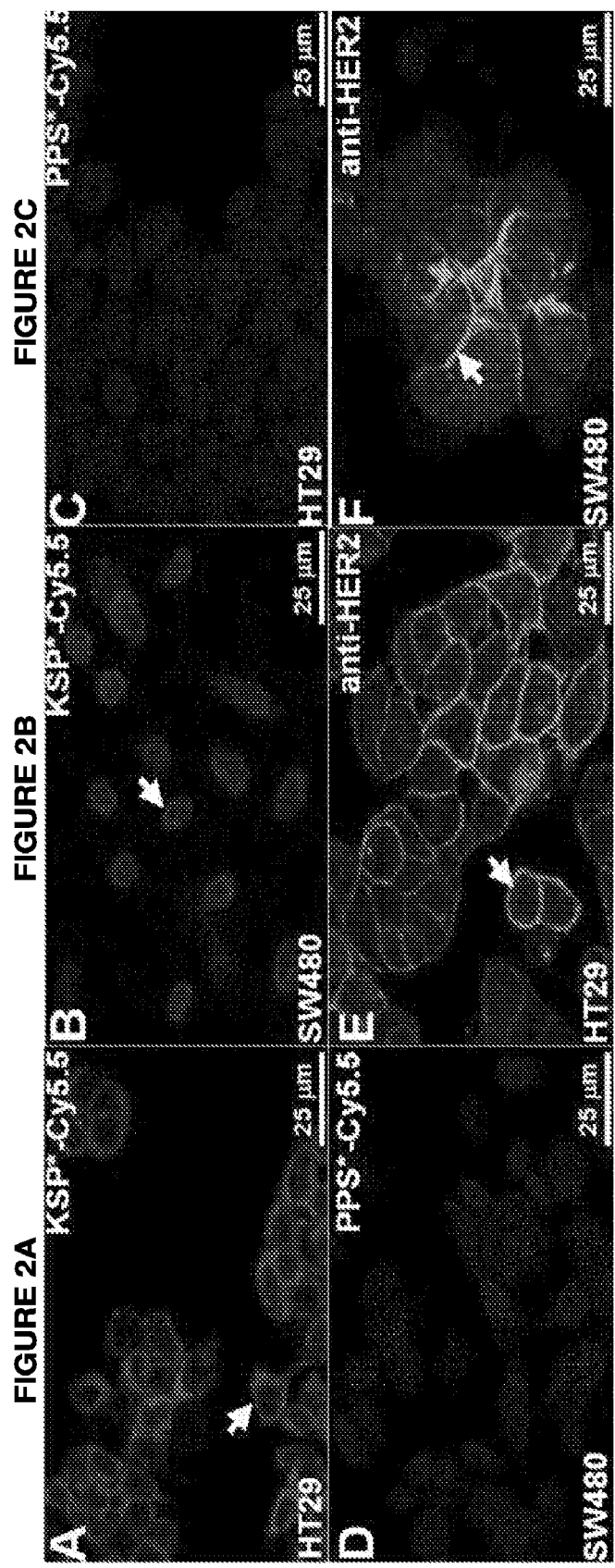

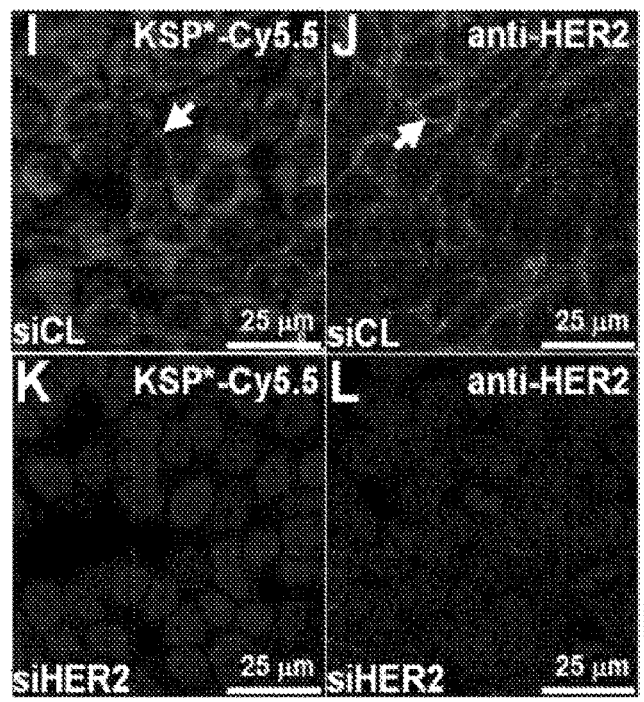
FIGURE 2I  FIGURE 2J
FIGURE 2K  FIGURE 2L
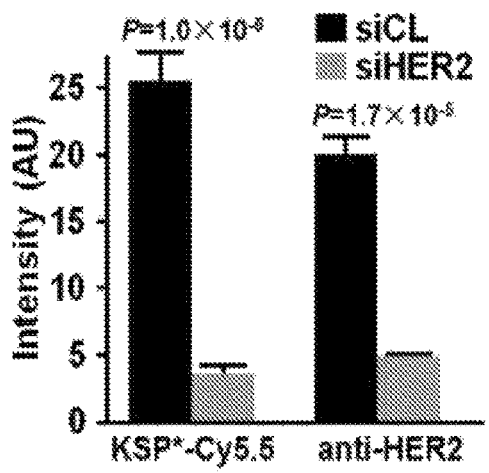
FIGURE 2M
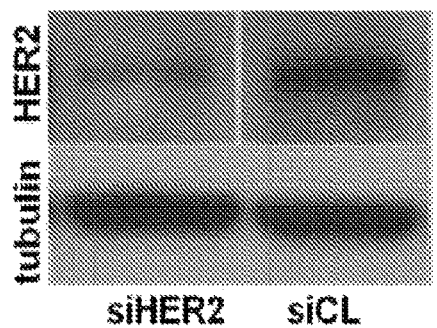
FIGURE 2N
FIGURE 2O

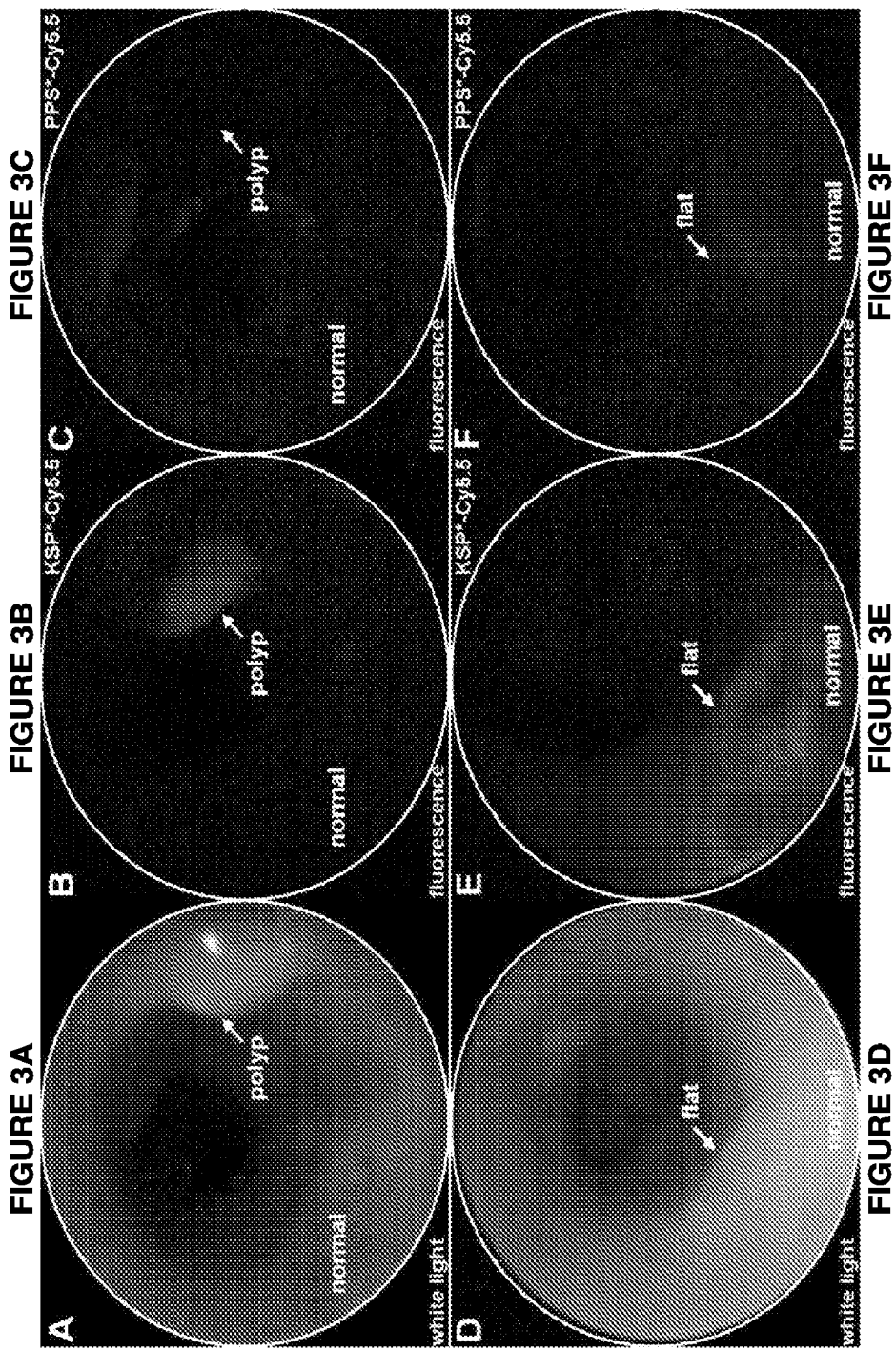

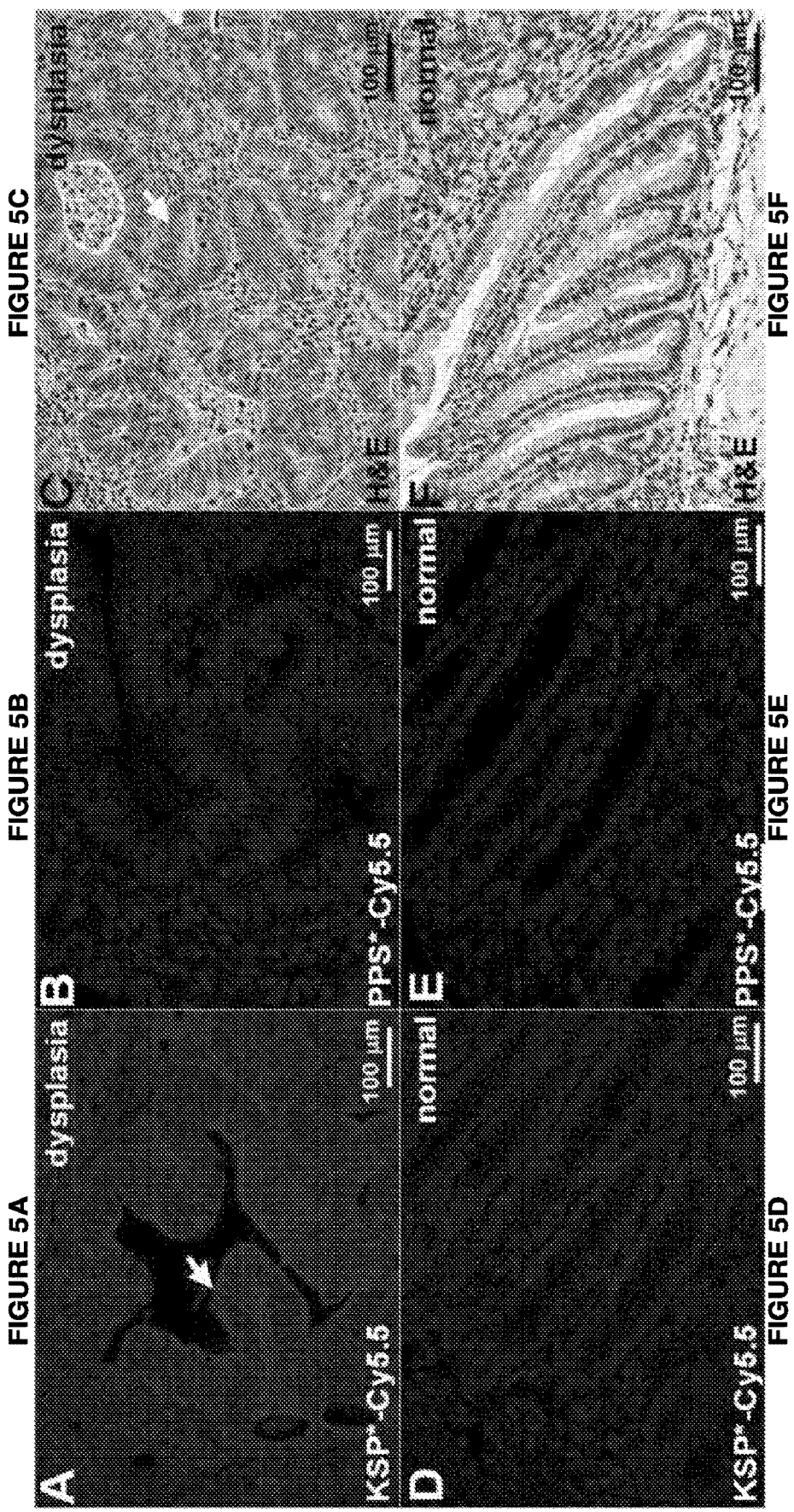

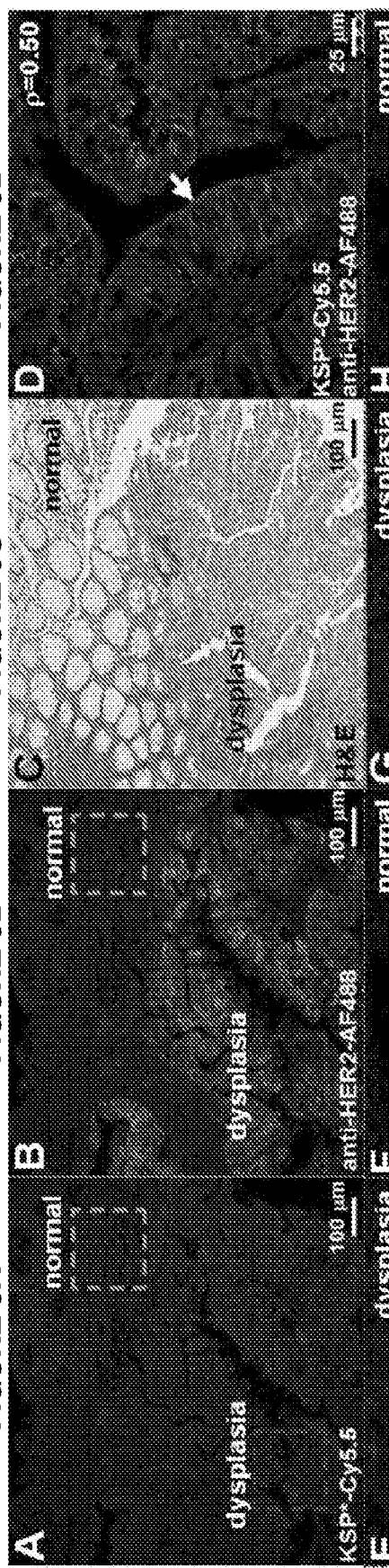

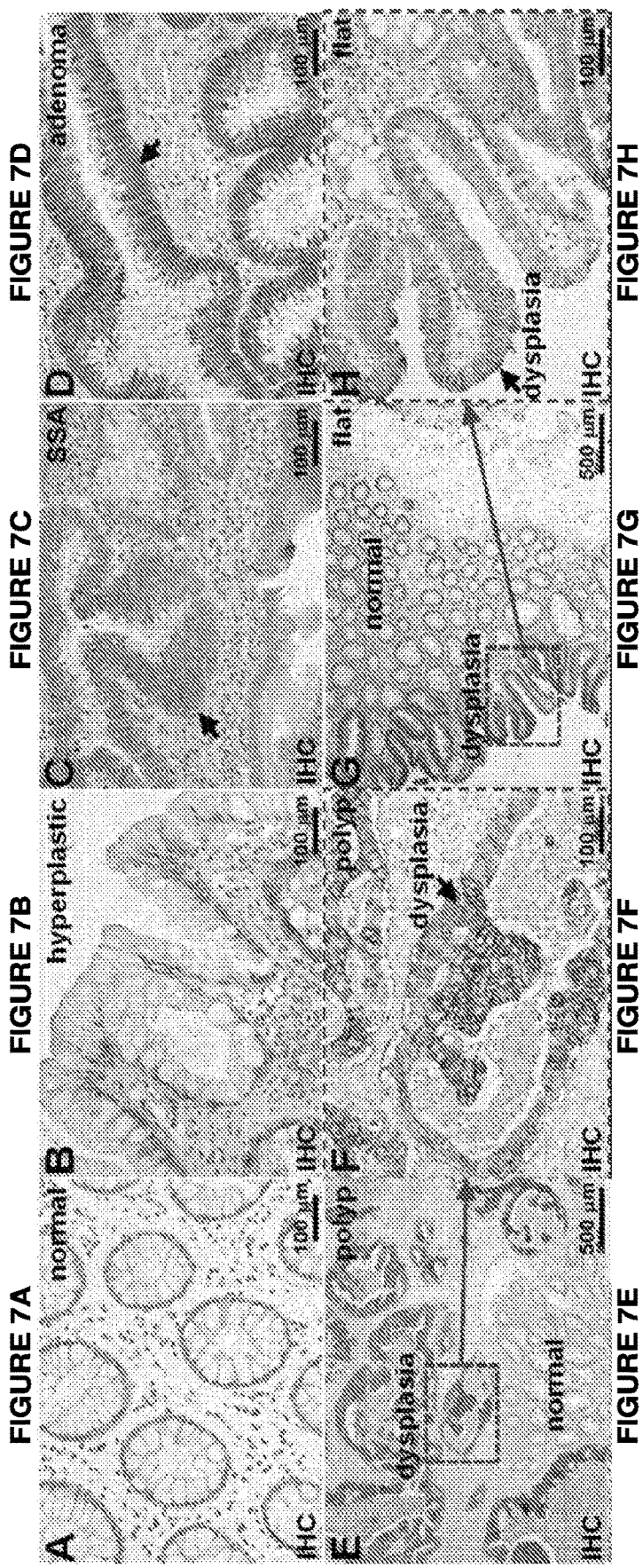

| Pathology \ IHC | 0+ | | 1+ | | 2+ | | 3+ | |
|---|---|---|---|---|---|---|---|---|
| normal | 30/30 | 100% | 0/30 | 0% | 0/30 | 0% | 0/30 | 0% |
| hyperplastic polyp | 6/12 | 50% | 3/12 | 25% | 3/12 | 25% | 0/12 | 0% |
| SSA | 8/14 | 57% | 4/14 | 29% | 2/14 | 14% | 0/14 | 0% |
| sporadic adenoma | 6/29 | 21% | 11/29 | 38% | 7/29 | 24% | 5/29 | 17% |

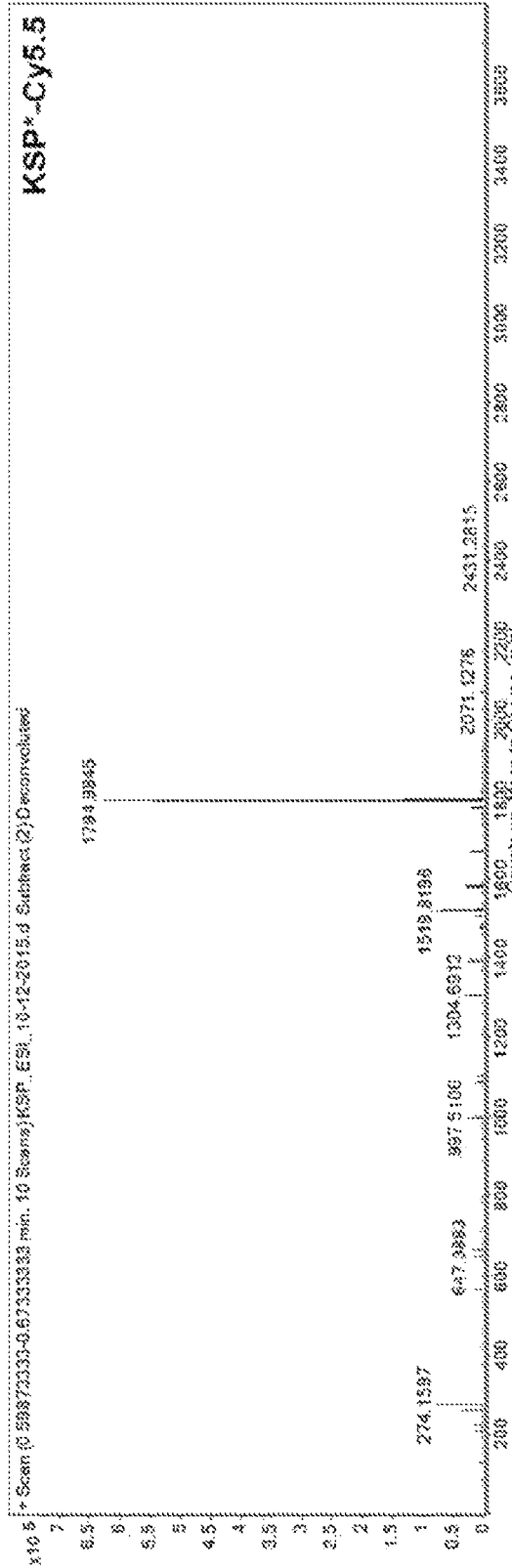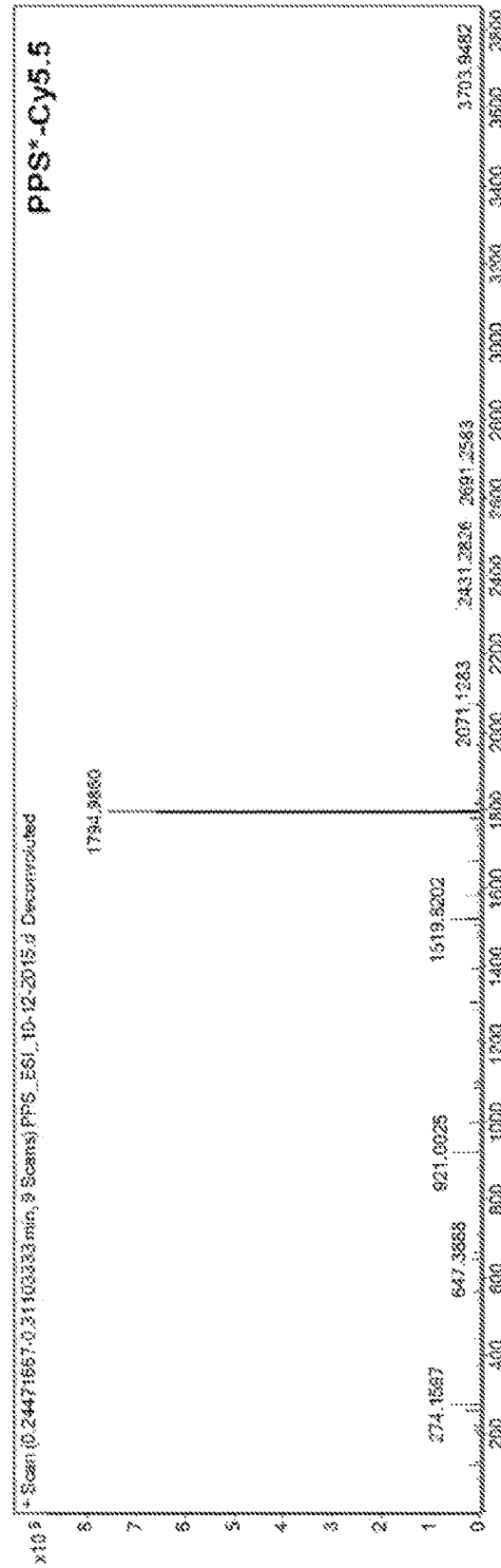
FIGURE 8A
FIGURE 8B

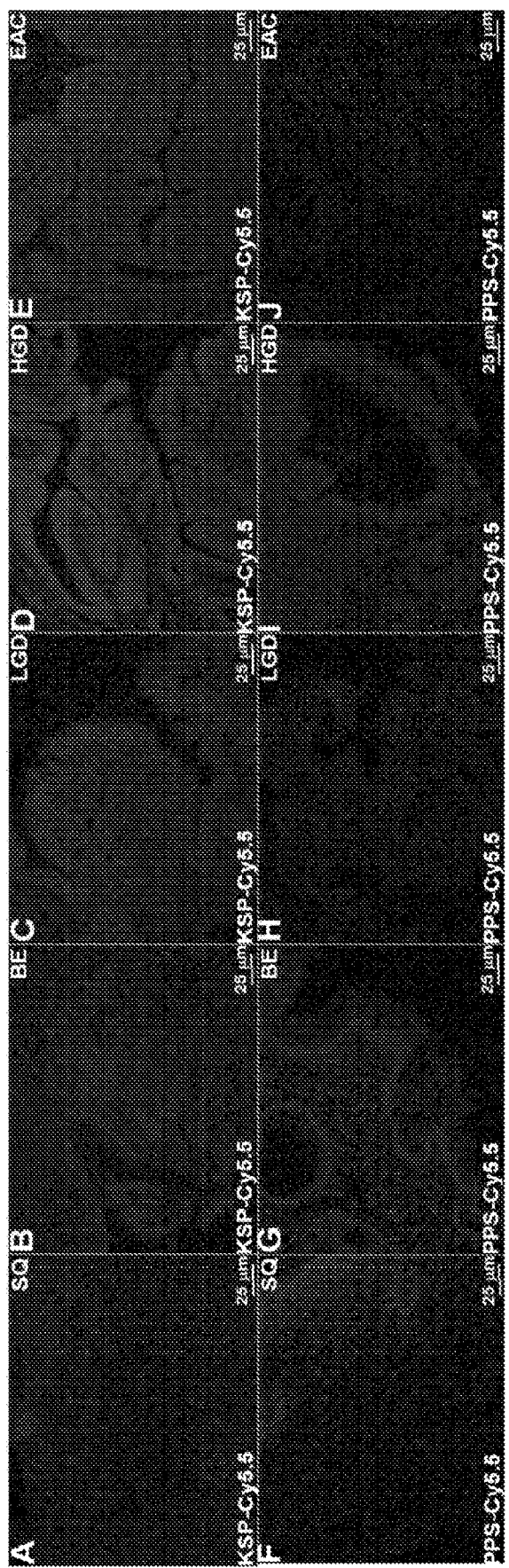

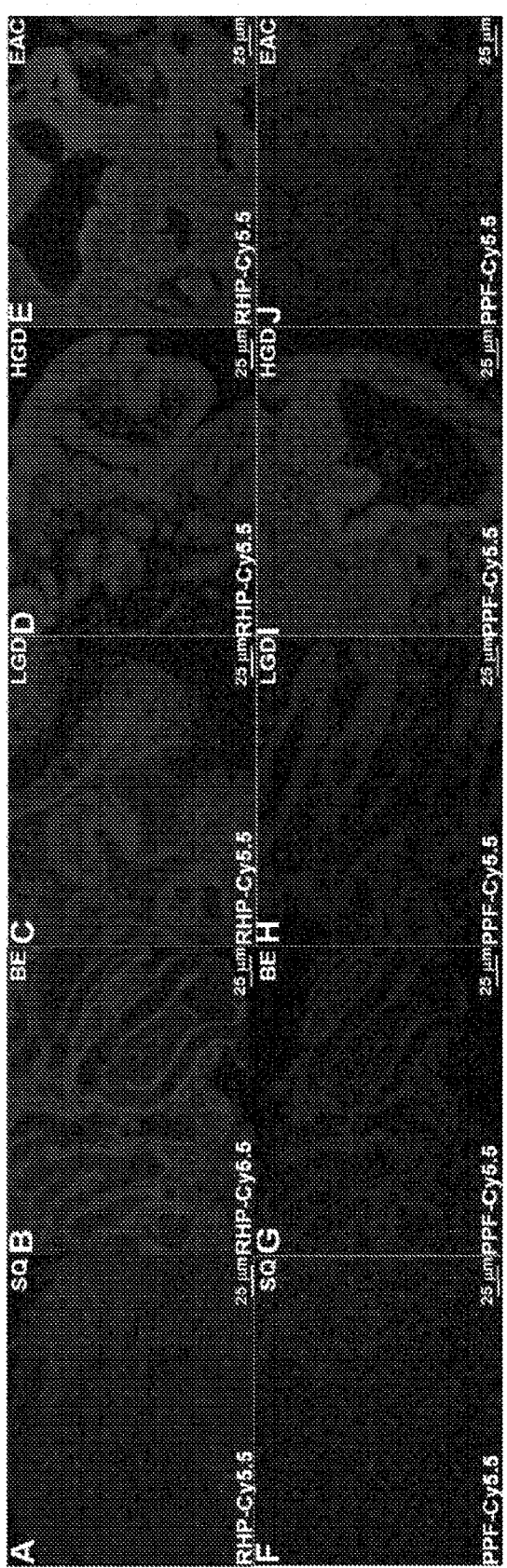

HER2 PEPTIDE REGENTS AND METHODS

CROSS REFERENCE TO RELATED APPLICATIONS

This application claims the benefit of U.S. Provisional Patent Application Ser. No. 62/262,159, filed Dec. 2, 2015, which is incorporated herein by reference in its entirety.

STATEMENT OF GOVERNMENT INTEREST

This invention was made with government support under U54 CA163059 awarded by the National Institutes of Health. The government has certain rights in the invention.

INCORPORATION BY REFERENCE OF MATERIAL SUBMITTED ELECTRONICALLY

This application contains, as a separate part of disclosure, a Sequence Listing in computer-readable form (filename: 50184PCT_SeqListing.txt; 1,629 bytes—ASCII text file created Dec. 1, 2016) which is incorporated by reference herein in its entirety.

FIELD

The present disclosure is directed to HER2-specific peptide reagents, methods for detecting pre-cancer, early cancer, and cancer using the peptide reagents, and methods for targeting precancerous cells, early cancer cells and cancerous cells using the peptide reagents.

BACKGROUND

Colorectal cancer (CRC) is one of the most common causes of cancer-related deaths in the world. Approximately 1,360,000 new cases were diagnosed globally in 2012, resulting in ~693,000 annual deaths. These numbers are expected to nearly double over the next 20 years with a rapid rise in obesity and more developing countries adopting a Western diet. Greater focus on early detection of pre-malignant lesions (dysplasia) is needed [Vogelstein et al., Science, 339: 1546-1558 (2013)].

Breast cancer is the most common cancer in women worldwide. It is estimated that more than 1.7 million new cases of breast cancer occurred among women in 2012. Amplification or over-expression of HER2 occurs in approximately 15-30% of breast cancers [Mitri et al., Chemother Res Pract, 743:193 (2012)].

Every year more than 450,000 new cases of esophageal adenocarcinoma (EAC) are diagnosed worldwide, and greater than 400,000 people will die from this disease. Over the past three decades, the incidence of esophageal cancer has risen faster than any other cancer in developed countries. EAC has poor prognosis thus early cancer detection is critical. This disease is thought to arise from Barrett's esophagus (BE), a pre-malignant condition whereby normal squamous is replaced by metaplastic columnar epithelium. BE is becoming more common in industrialized societies as a result of a rapid rise in obesity and acid reflux. BE is believed to transform into low-grade dysplasia (LGD) and progress sequentially to high-grade dysplasia (HGD) followed by EAC. On endoscopy, dysplasia may be flat in architecture and patchy in distribution. White light endoscopy with random 4-quadrant biopsy is recommended for surveillance, but is prone to sampling errors and false negatives. This protocol has sensitivity ranging from 28% to 85% and specificity ranging from 56% to 100% for detection of HGD and early EAC. Consequently, these guidelines are not wide practiced by community physicians. Surveillance endoscopy is recommended every 1 to 2 years. However, the incidence for finding HGD/EAC is quite low, and most patients have many biopsies collected with no evidence of neoplasia on pathology. The risk for developing cancer may be as low as ~0.12% per year in some patient poplulations. New imaging methods that rapidly visualize over expressed molecular targets may more effectively detect dysplasia, minimize biopsies, and reduce the frequency and cost for surveillance.

Cholangiocarcinoma (bile duct cancer) is the most common malignancy of the biliary tract, and is increasing in incidence and mortality worldwide. This disease is usually diagnosed at an advanced stage when the prognosis is poor. Biliary intraepithelial neoplasia (BilIN) represents a precursor condition, and if detected accurately, patients can undergo surgical resection with excellent outcomes. Patients suspected of having cholangiocarcinoma, frequently present with indeterminate biliary strictures found on transabdominal imaging. However, this finding is non-specific, and could represent either malignant or benign disease. [Shaib et al., Semin Liver Dis, 24: 115-125 (2004)]. Because biliary ducts are small in size, the amount of cells and tissues that can be obtained for either cytology or histology is usually insufficient to make a definitive diagnosis. Patients often delay therapy or undergo major surgery only to find benign strictures or late stage cancer. New methods of imaging are needed to identify early cholangiocarcinoma accurately in indeterminate biliary strictures to guide the physician in making therapeutic decisions.

Almost one million new cases of stomach cancer were estimated to have occurred in 2012 (952,000 cases, 6.8% of the total), making it the fifth most common malignancy in the world. Stomach cancer is the third leading cause of cancer death in both sexes worldwide (723,000 deaths, 8.8% of the total) [International Agency for Research on Cancer (IARC) and World Health Organization (WHO). GLOBO-CAN 2012: Estimated cancer incidence, mortality and prevalence worldwide in 2012].

Endoscopy is a frequently performed imaging exam that is widely accepted by patients and referring physicians. However, a significant miss rate of >25% has been found on back-to-back exams for grossly visible adenomatous polyps. Moreover, flat lesions can give rise to carcinoma, and has been found to be as high as 36% of all adenomas. Flat lesions have been found to be more aggressive than polyps, and five times more likely to harbor either in situ or submucosal carcinoma in some patient populations. Studies of outcomes also show that colonoscopy results in a minimal reduction in mortality for cancers that arise in the proximal colon (right side). Furthermore, cancer diagnosed after a "negative" colonoscopy occurs more frequently in the proximal colon. These findings have been attributed to greater genetic instability and a flat morphology. Thus, imaging methods that are sensitive to flat lesions may improve detection and prevention of CRC. Although colonoscopy is widely performed for screening, there is minimal reduction in mortality for carcinomas that arise in the proximal colon. Furthermore, cancer diagnosed after a "negative" colonoscopy occurs more frequently in the proximal colon. These findings have been attributed to greater microsatellite instability and a flat morphology.

Endoscopic imaging with use of exogenous fluorescent-labeled probes, is a promising method for achieving greater specificity in the detection of neoplastic lesions by identifying the expression of unique molecular targets. Imaging provides precise localization, and fluorescence provides improved contrast. Previously, several diagnostic molecules have been used as targeted agents, including antibodies and antibody fragments, for the detection of pre-malignant and malignant lesions in various types of cancer. However, the use of antibodies and antibody fragments is limited by immunogenicity, cost of production and long plasma half-life. Small molecules, RNA aptamers, and activatable probes have also been used. Peptides represent a new class of imaging agent that is compatible with clinical use in the digestive tract, in particular with topical administration.

Human epidermal growth factor receptor 2 (HER2, also known as ErbB2) is a member of the tyrosine kinase family that also includes HER1 (EGFR), HER3 and HER4, and is located on chromosome 17q21 [Brandt-Rauf et al., *Critical Reviews in Oncogenesis,* 5: 313-329 (1994); Tao and Maruyama, *Journal of Cell Science,* 121:3207-3217 (2008); Baselga and Swain, *Nature Reviews Cancer,* 9: 463-475 (2009)]. It encodes a 185 kDa transmembrane protein that lacks a natural ligand and functions as a co-receptor to form homo- and hetero-dimers with other HER family members. Dimerization results in the activation of signaling cascades that include the MAPK and PI3K/AKT pathways which are essential for cell proliferation and differentiation [Katz et al., *Biochim Biophys Acta.,* 1773(8): 1161-1176 (2007); Fornaro et al., *Nature Reviews Gastroenterology and Hepatology,* 8(7): 369-383 (2011)]. There is evidence that HER2 is highly over expressed in many types of tumors. Amplification and/or overexpression of this gene has been associated with mitogenesis, malignant transformation, increased cell motility, invasion and metastasis [Ross, *Cancer Invest.,* 19(5):554-68 (2001); Seo et al., *PLoS ONE,* 9(5): e98528 (2014); Khelwatty et al., *PLoS ONE,* 9(3): e91139 (2014)].

Several HER2 specific antibodies and antibody fragments have been used for optical and nuclear imaging, but are limited by slow binding kinetics, and have half-lives ranging from several hours to days that limit their clinical use. They are also are much more difficult to generate in large quantity, and have unacceptably high costs, limiting widespread clinical use for in vivo imaging. Peptides specific for HER2 and having higher binding affinities have been reported to be used for SPECT imaging [Larimer et al., *Mol Imaging Biol,* 16: 449-458 (2014); Geng, Theranostics 5: 1154-1165 (2015)], these required a highly sensitive imaging system for detection.

New products and methods for early detection of pre-cancer (dysplasia), early cancer and cancer are needed in the art. New products and methods for early detection would have important clinical applications for increasing the survival rate for CRC and other epithelial cell-derived cancers, and for reducing the healthcare costs.

SUMMARY

In one aspect, the disclosure provides a reagent consisting essentially of a peptide KSPNPRF (SEQ ID NO: 1), RHPF-PRF (SEQ ID NO: 2), RHPWPNR (SEQ ID NO: 3), RHPYPQR (SEQ ID NO: 4) or RKPFPRH (SEQ ID NO: 5), or a multimer form of the peptide, wherein the reagent specifically binds to HER2. In some embodiments, the multimer form is a dimer.

In some embodiments, the reagent comprises at least one detectable label attached to the peptide or multimer form of the peptide. In some embodiments, the multimer form is a dimer. In some embodiments, the detectable label is detectable by microscopy, photoacoustic, ultrasound, positron emission tomography (PET), single photon emission computed tomography (SPECT) or magnetic resonance imaging. In some embodiments, the label detectable by microscopy is fluorescein isothiocyanate (FITC), Cy5, Cy5.5, or IRDYE800. In some embodiments, the detectable label is attached to the peptide by a peptide linker. In some embodiments, the terminal amino acid of the linker is lysine. In some embodiment, the linker comprises the sequence GGGSK set out in SEQ ID NO: 6.

In some embodiments, the reagent comprises at least one therapeutic moiety attached to the peptide or multimer form of the peptide. In some embodiments, the therapeutic moiety is chemotherapeutic agent.

In some embodiments, the regent comprises at least one detectable label attached to the peptide or multimer form of the peptide and at least one therapeutic moiety attached to the peptide or multimer form of the peptide.

In another aspect, the disclosure provides a composition comprising a reagent of the disclosure and a pharmaceutically acceptable excipient.

In yet another aspect, the disclosure provides methods for detecting colon dysplasia in a patient comprising the steps of administering a reagent of the disclosure to the patient and detecting binding of the reagent to dysplastic colon cells. The disclosure also provides methods for detecting early colon cancer in a patient comprising the steps of administering a reagent of the disclosure to the patient and detecting binding of the reagent to early cancer cells in the colon. The disclosure also provides methods for detecting colon cancer in a patient comprising the steps of administering a reagent of the disclosure to the patient and detecting binding of the reagent to cancer cells in the colon.

In still another aspect, the disclosure provides methods for detecting dysplasia in a patient comprising the steps of administering a reagent of the disclosure to the patient and detecting binding of the reagent to dysplastic cells. The disclosure also provides methods for detecting early cancer in a patient comprising the steps of administering a reagent of the disclosure to the patient and detecting binding of the reagent to early cancer cells. The disclosure also provides methods for detecting cancer in a patient comprising the steps of administering a reagent of the disclosure to the patient and detecting binding of the reagent to cancer cells.

In another aspect, the disclosure provides a method of determining the effectiveness of a treatment for cancer and/or cancer metastasis, or recurrence of cancer in a patient comprising the step of administering a reagent of the disclosure to the patient, visualizing a first amount of cells labeled with the reagent, and comparing the first amount to a previously-visualized second amount of cells labeled with the reagent, wherein a decrease in the first amount cells labeled relative to the previously-visualized second amount of cells labeled is indicative of effective treatment. In some embodiments, the methods further comprise obtaining a biopsy of the cells labeled by the reagent.

In yet another aspect, the disclosure provides a method for delivering a therapeutic moiety to dysplastic cells of a patient comprising the step of administering a reagent of the disclosure to the patient.

In still another aspect, the disclosure provides a method for delivering a therapeutic moiety to early cancer cells of a patient comprising the step of administering a reagent of the disclosure to the patient.

In still another aspect, the disclosure provides a method for delivering a therapeutic moiety to cancer cells of a patient comprising the step of administering a reagent of the disclosure to the patient.

In the methods of each aspect described herein, dysplasia, early cancer or cancer arising from epithelial cells in, for example, colon, cervix, squamous cell, thyroid, brain, breast, ovary, prostate, liver, lung, esophagus, stomach, bladder, biliary tract, pancreas, oral cavity and skin is specifically contemplated.

In a further aspect, the disclosure provides a kit for administering a composition of the disclosure to a patient in need thereof, comprising the composition, instructions for use of the composition and a device for administering the composition to the patient.

In another aspect, the disclosure provides a peptide consisting of the amino acid sequence KSPNPRF (SEQ ID NO: 1), RHPFPRF (SEQ ID NO: 2) RHPWPNR (SEQ ID NO: 3), RHPYPQR (SEQ ID NO: 4) or RKPFPRH (SEQ ID NO: 5).

BRIEF DESCRIPTION OF THE DRAWINGS

FIG. 7—Overexpression of HER2 in human proximal colonic neoplasia. On immunohistochemistry (IHC) of archived specimens, minimal staining was observed from all sections of A) normal colon and most sections of B) hyperplastic polyps. Intense cell surface staining was seen from some C) sessile serrated adenomas (SSA) and D) many sporadic adenomas. E) Differences in HER2 expression between dysplastic and normal crypts from a polypoid adenoma can be seen. F) Magnified view from dashed red box in E) shows intense staining (arrow) of dysplastic colonocytes. G) Difference in staining between dysplastic and normal crypts is shown for flat adenoma. H) Magnified view from dashed red box in G). I) No antibody (control). J) Consensus between 2 GI pathologists using a standard IHC scoring system revealed overexpression, defined by either 2+ or 3+ staining, in 0% (0/30) of normal, 25% (3/12) of hyperplastic polyps, 14% (2/14) of SSA, and 41% (12/29) of adenomas.

FIG. 8—Mass spectrometry of Cy5.5-labeled peptide reagents. We measured an experimental mass-to-charge (m/z) ratio on mass spectrometry of 1794.98 for both KSP*-Cy5.5 and PPS*-Cy5.5, which agrees with expected values.

FIG. 12—Specific binding of KSP*-Cy5.5 peptide reagent to ErbB2 (HER2) overexpressed in human Barrett's esophagus. Increasing fluorescence intensity is observed for staining of A-E) KSP-Cy5.5 peptide reagent with cancer progression in Barrett's esophagus on excised human specimens. F-J) Minimal staining is observed with PPS*-Cy5.5, a scrambled peptide reagent used for control. Key: SQ—squamous, BE—Barrett's esophagus, LGD—low-grade dysplasia, HGD—high-grade dysplasia, EAC—esophageal adenocarcinoma.

FIG. 13—Specific binding of RHP*-Cy5.5 peptide reagent to ErbB2 (HER2) overexpressed in human Barrett's esophagus. Increasing fluorescence intensity is observed for staining of A-E) RHP*-Cy5.5 peptide reagent with cancer progression in Barrett's esophagus on excised human specimens. F-J) Minimal staining is observed with PPF*-Cy5.5, a scrambled peptide reagent used for control. Key: SQ—squamous, BE—Barrett's esophagus, LGD—low-grade dysplasia, HGD—high-grade dysplasia, EAC—esophageal adenocarcinoma.

DESCRIPTION

Figure 1A:
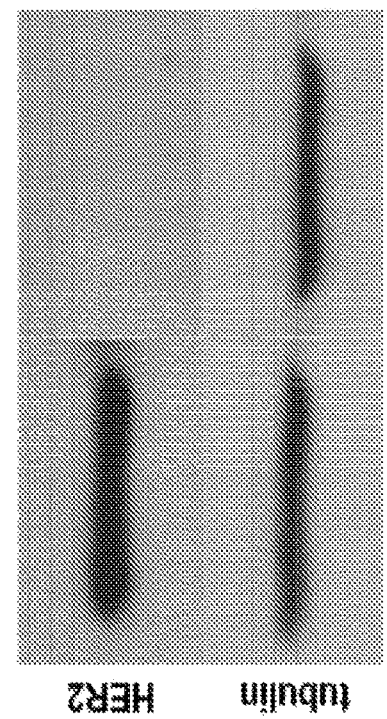
FIG. 1—Selection of peptide specific for HER2. A) A structural model (2A91) of HER2-ECD was used to evaluate binding interactions between this target and candidate peptides. The top 5 candidates were FITC-labeled, and binding was evaluated with confocal microscopy in vitro. B) Western blot of Flo1-HER2 and Q-hTERT (control) cells show difference in HER2 expression. C) KSPNPRF (PEP1) (SEQ ID NO: 1) showed highest mean fluorescence intensity compared with other peptide candidates with Flo1-HER2 relative to Q-hTERT cells. Data was transformed to log base 2. D) Chemical structure of KSPNPRF peptide (black) (SEQ ID NO: 1) labeled with Cy5.5 fluorophore (red) via a GGGSK linker (blue) (SEQ ID NO: 6); KSP*-Cy5.5. E) Scrambled control peptide PPSNFKR; PPS*-Cy5.5. For both peptides, F) peak absorption occurs at $\lambda_{ex}$=671 nm and G) the fluorescence spectra show maximum emission near 708 nm in the NIR.

Transformed cells and tissues express molecular changes well in advance of gross morphological changes, thus providing a unique opportunity for the early detection of cancer. Peptides that bind to pre-cancerous lesions have the potential to guide tissue biopsy for lesions that are endoscopically "invisible." Peptides have in vivo advantages because they can be delivered topically to identify early molecular changes on the surface of epithelial cells where cancer originates. In addition, they can exhibit rapid binding kinetics and also diffuse into diseased tissue.

In one aspect, the disclosure provides peptides that specifically bind to HER2. HER2 is expressed on dysplastic cells and/or cancerous cells. "Cancerous cells" herein include early cancer and cancer cells. The peptides include, but are not limited to, the peptides KSPNPRF (SEQ ID NO: 1), RHPFPRF (SEQ ID NO: 2), RHPWPNR (SEQ ID NO: 3), RHPYPQR (SEQ ID NO: 4) and RKPFPRH (SEQ ID NO: 5).

In a further aspect, the disclosure provides reagents comprising a peptide of the disclosure. A "reagent" as used herein comprises at least two components, a peptide of the disclosure and another moiety attached to the peptide. The only component of the reagent that contributes to binding of HER2 is the peptide of the disclosure. In other words, the reagent "consists essentially of" a peptide of the disclosure. In some embodiments, the other moiety comprises amino acids but the peptide of the disclosure is not linked to those amino acids in nature and the other amino acids do not affect binding of the peptide to HER2. Moreover, the other moiety in a reagent contemplated herein is not a phage in a phage display library or a component of any other type of peptide display library.

In some embodiments, the reagents comprise at least one detectable label as a moiety attached to a peptide of the disclosure. The detectable label may be detectable, for example, by microscopy, ultrasound, PET, SPECT, or magnetic resonance imaging. In some embodiments the label detectable by microscopy is fluorescein isothiocyanate (FITC), Cy5, Cy5.5 and IRdye800.

In some embodiments, the detectable label is attached to a peptide of the disclosure by a peptide linker. The terminal amino acid of the linker may be a lysine such as in the exemplary linker GGGSK (SEQ ID NO: 6).

In some embodiments, the reagents comprise at least one therapeutic moiety attached to a peptide of the disclosure. The therapeutic moiety may be a chemopreventative or chemotherapeutic agent. In certain embodiments, the therapeutic moiety is celecoxib, 5-fluorouracil, and/or chlorambucil.

In some embodiments, the regent comprises at least one detectable label attached to the peptide or multimer form of the peptide, and at least one therapeutic moiety attached to the peptide or multimer form of the peptide.

In yet a further aspect, the disclosure provides a composition comprising a reagent of the disclosure and a pharmaceutically acceptable excipient.

In still a further aspect, the disclosure provides a method for specifically detecting pre-cancer (dysplasia), early cancer and/or cancer in a patient comprising the steps of administering a reagent of the disclosure attached to a detectable label to the patient and detecting binding of the reagent to dysplastic cells or early cancer cells. In some embodiments, the detectable binding takes place in vivo. In others, the detectable binding takes places in vitro. In still others, the detectable binding takes place in situ. Detection of pre-cancer (dysplasia), early cancer and/or cancer arising from epithelial cells is specifically contemplated. Dysplasia, early cancer or cancer arising from epithelial cells in, for example, colon, cervix, squamous cell, thyroid, brain, breast, ovary, prostate, liver, lung, esophagus, stomach, bladder, biliary tract, pancreas, oral cavity and skin is specifically contemplated.

The phrases "specifically binds" and "specifically detects" a cell mean herein that the reagent binds to and/or is detected in association with a cell expressing HER2, and the reagent does not bind to and is not detected in association with another type of cell at the level of sensitivity at which the method is carried out.

In the colon, for example, the transformation from pre-malignant mucosa to carcinoma involves the development of flat and depressed (non-polypoid) lesions, adenomatous polyps (polypoid lesions) and then frank carcinoma (colon cancer cells). Detecting colon dysplasia (i.e., dysplastic cells), pre-cancerous cells and/or cancerous according to the disclosure includes detecting binding to flat and depressed lesions, adenomatous polyps and/or cancer cells. In some embodiments, a reagent of the disclosure specifically detects cells of flat and depressed lesions. In some embodiments, a reagent of the disclosure specifically detects cells of adenomatous polyps. In some embodiments, a reagent of the disclosure specifically detects colon cancer cells. In some embodiments, a reagent of the disclosure may specifically detect two or more of cells of flat and depressed lesions, cells of adenomatous polyps and colon cancer cells.

Flat dysplastic lesions are also observed in the setting of chronic ulcerative colitis and are also contemplated to be detectable by methods of the disclosure.

In an additional aspect, the disclosure provides a method of determining the effectiveness of a treatment for cancer and/or cancer metastasis, or recurrence of cancer in a patient comprising the step of administering a reagent of the disclosure attached to a detectable label to the patient, visualizing a first amount of cells labeled with the reagent, and comparing the first amount to a previously-visualized second amount of cells labeled with the reagent, wherein a decrease in the first amount cells labeled relative to the previously-visualized second amount of cells labeled is indicative of effective treatment. In some embodiments, a decrease of 5% is indicative of effective treatment. In other embodiments, a decrease of about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or more is indicative of effective treatment. In some embodiments, the method further comprises obtaining a biopsy of the cells labeled by the reagent.

In another aspect, the disclosure provides a method for delivering a therapeutic moiety to a patient comprising the step of administering a reagent of the disclosure attached to a therapeutic moiety to the patient.

In yet another aspect, the disclosure provides a method for delivering a therapeutic moiety to a patient comprising the step of administering a reagent of the disclosure attached to a therapeutic moiety to the colon of the patient.

In still another aspect, the disclosure provides a kit for administering a composition of the disclosure to a patient in need thereof, where the kit comprises a composition of disclosure, instructions for use of the composition and a device for administering the composition to the patient.

Linkers, Peptides and Peptide Analogs

As used herein, a "linker" is a sequence of amino acids located at the C-terminus of a peptide of the disclosure. In some embodiments, the linker sequence terminates with a lysine residue.

In some embodiments, the presence of a linker results in at least a 1% increase in detectable binding of a reagent of the disclosure to dysplastic colon cells or cancerous colon cells compared to the detectable binding of the reagent in the absence of the linker. In various aspects, the increase in detectable binding is at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 25-fold, at least about 30-fold, at least about 35-fold, at least about 40-fold, at least about 45-fold, at least about 50-fold, at least about 100-fold or more.

The term "peptide" refers to molecules of 2 to 50 amino acids, molecules of 3 to 20 amino acids, and those of 6 to 15 amino acids. Peptides and linkers as contemplated by the disclosure may be 5 amino acids in length. In various aspects, a polypeptide or linker may be 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more amino acids in length.

Exemplary peptides are, in various aspects, randomly generated by methods known in the art, carried in a polypeptide library (for example and without limitation, a phage display library), derived by digestion of proteins, or chemically synthesized. Peptides exemplified in the present disclosure have been developed using techniques of phage display, a powerful combinatorial method that uses recombinant DNA technology to generate a complex library of polypeptides for selection by preferential binding to cell surface targets [Scott et al., *Science*, 249:386-390 (1990)]. The protein coat of bacteriophage, such as the filamentous M13 or icosahedral T7, is genetically engineered to express a very large number ($>10^9$) of different polypeptides with unique sequences to achieve affinity binding [Cwirla et al., *Proc. Natl. Acad. Sci. USA*, 87:6378-6382 (1990)]. Selection is then performed by biopanning the phage library against cultured cells and tissues that over express the target. The DNA sequences of these candidate phage are then recovered and used to synthesize the polypeptide [Pasqualini et al., *Nature*, 380:364-366 (1996)]. The polypeptides that preferentially bind to dysplastic mucosa are optionally labeled with fluorescence dyes, including but not limited to, FITC, Cy 5.5, Cy 7, and Li-Cor. These polypeptide-dye reagents have been developed and have demonstrated preferential binding to colon cancer (HT29) cells in culture and to pre-clinical xenograft models [Kelly et al., *Cancer Res.*, 64:6247-51 (2004)].

Peptides include D and L forms, either purified or in a mixture of the two forms. Also contemplated by the present disclosure are peptides that compete with peptides of the disclosure for binding to colon cells.

In some embodiments, a peptide of a reagent of the disclosure is presented in multimer form. Various scaffolds are known in the art upon which multiple peptides can be presented. In some embodiments, a peptide is presented in multimer form on a trilysine dendritic wedge. In some embodiments, a peptide is presented in dimer form using a linker including, but not limited to, an aminohexanoic acid linker. Other scaffolds known in the art include, but are not limited to, other dendrimers and polymeric (e.g., PEG) scaffolds.

It will be understood that peptides and linkers of the disclosure optionally incorporate modifications known in the art and that the location and number of such modifications are varied to achieve an optimal effect in the peptide and/or linker analog.

In some embodiments, the compound is a peptide analog having a structure based on one of the peptides disclosed herein (the "parent peptide") but differs from the parent peptide in one or more respects. Accordingly, as appreciated by one of ordinary skill in the art, the teachings regarding the parent peptides provided herein may also be applicable to the peptide analogs.

In some embodiments, the peptide analog comprises the structure of a parent peptide, except that the peptide analog comprises one or more non-peptide bonds in place of peptide bond(s). In some embodiments, the peptide analog comprises in place of a peptide bond, an ester bond, an ether bond, a thioether bond, an amide bond, and the like. In some embodiments, the peptide analog is a depsipeptide comprising an ester linkage in place of a peptide bond.

In some embodiments, the peptide analog comprises the structure of a parent peptide described herein, except that the peptide analog comprises one or more amino acid substitutions, e.g., one or more conservative amino acid substitutions. Conservative amino acid substitutions are known in the art, and include amino acid substitutions in which one amino acid having certain physical and/or chemical properties is exchanged for another amino acid that has the same chemical or physical properties. For instance, the conservative amino acid substitution may be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

In some aspects, the peptide analog comprises one or more synthetic amino acids, e.g., an amino acid non-native to a mammal. Synthetic amino acids include β-alanine (β-Ala), N-α-methyl-alanine (Me-Ala), aminobutyric acid (Abu), γ-aminobutyric acid (γ-Abu), aminohexanoic acid (ε-Ahx), aminoisobutyric acid (Aib), aminomethylpyrrole carboxylic acid, aminopiperidinecarboxylic acid, aminoserine (Ams), aminotetrahydropyran-4-carboxylic acid, arginine N-methoxy-N-methyl amide, β-aspartic acid (β-Asp), azetidine carboxylic acid, 3-(2-benzothiazolyl)alanine, α-tert-butylglycine, 2-amino-5-ureido-n-valeric acid (citrulline, Cit), β-Cyclohexylalanine (Cha), acetamidomethylcysteine, diaminobutanoic acid (Dab), diaminopropionic acid (Dpr), dihydroxyphenylalanine (DOPA), dimethylthiazolidine (DMTA), γ-Glutamic acid (γ-Glu), homoserine (Hse), hydroxyproline (Hyp), isoleucine N-methoxy-N-methyl amide, methyl-isoleucine (MeIle), isonipecotic acid (Isn), methyl-leucine (MeLeu), methyl-lysine, dimethyl-lysine, trimethyl-lysine, methanoproline, methionine-sulfoxide (Met(O)), methionine-sulfone (Met(O$_2$)), norleucine (Nle), methyl-norleucine (Me-Nle), norvaline (Nva), ornithine (Orn), para-aminobenzoic acid (PABA), penicillamine (Pen), methylphenylalanine (MePhe), 4-Chlorophenylalanine (Phe(4-Cl)), 4-fluorophenylalanine (Phe(4-F)), 4-nitrophenylalanine (Phe(4-NO$_2$)), 4-cyanophenylalanine ((Phe (4-CN)), phenylglycine (Phg), piperidinylalanine, piperidinylglycine, 3,4-dehydroproline, pyrrolidinylalanine, sarcosine (Sar), selenocysteine (Sec), O-Benzyl-phosphoserine, 4-amino-3-hydroxy-6-methylheptanoic acid (Sta), 4-amino-5-cyclohexyl-3-hydroxypentanoic acid (ACHPA), 4-amino-3-hydroxy-5-phenylpentanoic acid (AHPPA), 1,2, 3,4,-tetrahydro-isoquinoline-3-carboxylic acid (Tic), tetrahydropyranglycine, thienylalanine (Thi), O-benzyl-phosphotyrosine, O-Phosphotyrosine, methoxytyrosine, ethoxytyrosine, O-(bis-dimethylamino-phosphono)-tyrosine, tyrosine sulfate tetrabutylamine, methyl-valine (Me-Val), and alkylated 3-mercaptopropionic acid.

In some embodiments, the peptide analog comprises one or more non-conservative amino acid substitutions and the peptide analog still functions to a similar extent, the same extent, or an improved extent as the parent peptide. In certain embodiments, the peptide analog comprising one or more non-conservative amino acid substitutions exhibits about the same or greater binding to dysplastic cells or early cancer cells in comparison to the parent peptide.

In some embodiments, the peptide analog comprises one or more amino acid insertions or deletions, in comparison to the parent peptide described herein. In some embodiments, the peptide analog comprises an insertion of one or more amino acids in comparison to the parent peptide. In some embodiments, the peptide analog comprises a deletion of one or more amino acids in comparison to the parent peptide. In some embodiments, the peptide analog comprises an insertion of one or more amino acids at the N- or C-terminus in comparison to the parent peptide. In some embodiments, the peptide analog comprises a deletion of one or more amino acids at the N- or C-terminus in comparison to the parent peptide. In these embodiments, the peptide analog still exhibits about the same or greater binding to dysplastic cells or early cancer cells in comparison to the parent peptide.

Detectable Markers

As used herein, a "detectable marker" is any label that can be used to identify the binding of a composition of the disclosure to dysplastic cells or early cancer cells. Non-limiting examples of detectable markers are fluorophores, chemical or protein tags that enable the visualization of a polypeptide. Visualization in certain aspects is carried out with the naked eye, or a device (for example and without limitation, an endoscope) and may also involve an alternate light or energy source.

Fluorophores, chemical and protein tags that are contemplated for use in the disclosure include, but are not limited to, FITC, Cy 5.5, Cy 7, Li-Cor, a radiolabel, biotin, luciferase, 1,8-ANS (1-Anilinonaphthalene-8-sulfonic acid), 1-Anilinonaphthalene-8-sulfonic acid (1,8-ANS), 5-(and-6)-Carboxy-2',7'-dichlorofluorescein pH 9.0, 5-FAM pH 9.0, 5-ROX (5-Carboxy-X-rhodamine, triethylammonium salt), 5-ROX pH 7.0, 5-TAMRA, 5-TAMRA pH 7.0, 5-TAMRA-MeOH, 6 JOE, 6,8-Difluoro-7-hydroxy-4-methylcoumarin pH 9.0, 6-Carboxyrhodamine 6G pH 7.0, 6-Carboxyrhodamine 6G, hydrochloride, 6-HEX, SE pH 9.0, 6-TET, SE pH 9.0, 7-Amino-4-methylcoumarin pH 7.0, 7-Hydroxy-4-methylcoumarin, 7-Hydroxy-4-methylcoumarin pH 9.0, Alexa 350, Alexa 405, Alexa 430, Alexa 488, Alexa 532, Alexa 546, Alexa 555, Alexa 568, Alexa 594, Alexa 647, Alexa 660, Alexa 680, Alexa 700, Alexa Fluor 430 antibody conjugate pH 7.2, Alexa Fluor 488 antibody conjugate pH 8.0, Alexa Fluor 488 hydrazide-water, Alexa Fluor 532 antibody conjugate pH 7.2, Alexa Fluor 555 antibody conjugate pH 7.2, Alexa Fluor 568 antibody conjugate pH 7.2, Alexa Fluor 610 R-phycoerythrin streptavidin pH 7.2, Alexa Fluor 647 antibody conjugate pH 7.2, Alexa Fluor 647 R-phycoerythrin streptavidin pH 7.2, Alexa Fluor 660 antibody conjugate pH 7.2, Alexa Fluor 680 antibody conjugate pH 7.2, Alexa Fluor 700 antibody conjugate pH 7.2, Allophycocyanin pH 7.5, AMCA conjugate, Amino Coumarin, APC (allophycocyanin), Atto 647, BCECF pH 5.5, BCECF pH 9.0, BFP (Blue Fluorescent Protein), Calcein, Calcein pH 9.0, Calcium Crimson, Calcium Crimson Ca2+, Calcium Green, Calcium Green-1 Ca2+, Calcium Orange, Calcium Orange Ca2+, Carboxynaphthofluorescein pH 10.0, Cascade Blue, Cascade Blue BSA pH 7.0, Cascade Yellow, Cascade Yellow antibody conjugate pH 8.0, CFDA, CFP (Cyan Fluorescent Protein), CI-NERF pH 2.5, CI-NERF pH 6.0, Citrine, Coumarin, Cy 2, Cy 3, Cy 3.5, Cy 5, C5.5, CyQUANT GR-DNA, Dansyl Cadaverine, Dansyl Cadaverine, MeOH, DAPI, DAPI-DNA, Dapoxyl (2-aminoethyl) sulfonamide, DDAO pH 9.0, Di-8 ANEPPS, Di-8-ANEPPS-lipid, DiI, DiO, DM-NERF pH 4.0, DM-NERF pH 7.0, DsRed, DTAF, dTomato, eCFP (Enhanced Cyan Fluorescent Protein), eGFP (Enhanced Green Fluorescent Protein), Eosin, Eosin antibody conjugate pH 8.0, Erythrosin-5-isothiocyanate pH 9.0, eYFP (Enhanced Yellow Fluorescent Protein), FDA, FITC antibody conjugate pH 8.0, FlAsH, Fluo-3, Fluo-3 Ca2+, Fluo-4, Fluor-Ruby, Fluorescein, Fluorescein 0.1 M NaOH, Fluorescein antibody conjugate pH 8.0, Fluorescein dextran pH 8.0, Fluorescein pH 9.0, Fluoro-Emerald, FM 1-43, FM 1-43 lipid, FM 4-64, FM 4-64, 2% CHAPS, Fura Red Ca2+, Fura Red, high Ca, Fura Red, low Ca, Fura-2 Ca2+, Fura-2, Fura-2, GFP (S65T), HcRed, Indo-1 Ca2+, Indo-1, Ca free, Indo-1, Ca saturated, JC-1, JC-1 pH 8.2, Lissamine rhodamine, Lucifer Yellow, CH, Magnesium Green, Magnesium Green Mg2+, Magnesium Orange, Marina Blue, mBanana, mCherry, mHoneydew, mOrange, mPlum, mRFP, mStrawberry, mTangerine, NBD-X, NBD-X, MeOH, NeuroTrace 500/525, green fluorescent Nissl stain-RNA, Nile Blue, Nile Red, Nile Red-lipid, Nissl, Oregon Green 488, Oregon Green 488 antibody conjugate pH 8.0, Oregon Green 514, Oregon Green 514 antibody conjugate pH 8.0, Pacific Blue, Pacific Blue antibody conjugate pH 8.0, Phycoerythrin, R-Phycoerythrin pH 7.5, ReAsH, Resorufin, Resorufin pH 9.0, Rhod-2, Rhod-2 Ca2+, Rhodamine, Rhodamine 110, Rhodamine 110 pH 7.0, Rhodamine 123, MeOH, Rhodamine Green, Rhodamine phalloidin pH 7.0, Rhodamine Red-X antibody conjugate pH 8.0, Rhodamine Green pH 7.0, Rhodol Green antibody conjugate pH 8.0, Sapphire, SBFI-Na+, Sodium Green Na+, Sulforhodamine 101, Tetramethylrhodamine antibody conjugate pH 8.0, Tetramethylrhodamine dextran pH 7.0, and Texas Red-X antibody conjugate pH 7.2.

Non-limiting examples of chemical tags contemplated by the disclosure include radiolabels. For example and without limitation, radiolabels that contemplated in the compositions and methods of the present disclosure include $^{11}C$, $^{13}N$, $^{15}O$, $^{18}F$, 18F-FDG, $^{32}P$, $^{52}Fe$, $^{62}Cu$, $^{64}Cu$, $^{67}Cu$, $^{67}Ga$, $^{68}Ga$, $^{86}Y$, $^{89}Zr$, $^{90}Y$, $^{94}mTc$, $^{94}Tc$, $^{95}Tc$, $^{99}mTc$, $^{109}Pd$, $^{111}Ag$, $^{111}In$, $^{123}I$, $^{124}I$, $^{125}I$, $^{131}I$, $^{140}La$, $^{149}Pm$, $^{153}Sm$, $^{154-159}Gd$, $^{165}Dy$, $^{166}Dy$, $^{166}Ho$, $^{169}Yb$, $^{175}Yb$, $^{175}Lu$, $^{177}Lu$, $^{186}Re$, $^{188}Re$, $^{192}Ir$, $^{198}Au$, $^{199}Au$, and $^{212}Bi$.

A worker of ordinary skill in the art will appreciate that there are many such detectable markers that can be used to visualize a cell, in vitro, in vivo or ex vivo.

Therapeutic Moieties

Therapeutic moieties contemplated by the disclosure include, but are not limited to polypeptides (including protein therapeutics) or peptides, small molecules, chemotherapeutic agents, or combinations thereof.

The term "small molecule", as used herein, refers to a chemical compound, for instance a peptidometic or oligonucleotide that may optionally be derivatized, or any other low molecular weight organic compound, either natural or synthetic.

By "low molecular weight" is meant compounds having a molecular weight of less than 1000 Daltons, typically between 300 and 700 Daltons. Low molecular weight compounds, in various aspects, are about 100, about 150, about 200, about 250, about 300, about 350, about 400, about 450, about 500, about 550, about 600, about 650, about 700, about 750, about 800, about 850, about 900, about 1000 or more Daltons.

In some embodiments, the therapeutic moiety is a protein therapeutic. Protein therapeutics include, without limitation, cellular or circulating proteins as well as fragments and derivatives thereof. Still other therapeutic moieties include polynucleotides, including without limitation, protein coding polynucleotides, polynucleotides encoding regulatory polynucleotides, and/or polynucleotides which are regulatory in themselves. Optionally, the compositions comprise a combination of the compounds described herein.

In some embodiments, protein therapeutics include cytokines or hematopoietic factors including without limitation IL-1 alpha, IL-1 beta, IL-2, IL-3, IL-4, IL-5, IL-6, IL-11, colony stimulating factor-1 (CSF-1), M-CSF, SCF, GM-CSF, granulocyte colony stimulating factor (G-CSF), EPO, interferon-alpha (IFN-alpha), consensus interferon, IFN-beta, IFN-gamma, IL-7, IL-8, IL-9, IL-10, IL-12, IL-13, IL-14, IL-15, IL-16, IL-17, IL-18, thrombopoietin (TPO), angiopoietins, for example Ang-1, Ang-2, Ang-4, Ang-Y, the human angiopoietin-like polypeptide, vascular endothelial growth factor (VEGF), angiogenin, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neutrophic factor, ciliary neutrophic factor receptor, cytokine-induced neutrophil chemotactic factor 1, cytokine-induced neutrophil, chemotactic factor 2α, cytokine-induced neutrophil chemotactic factor 2β, β endothelial cell growth factor, endothelin 1, epidermal growth factor, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor acidic, fibroblast growth factor basic, glial cell line-derived neutrophic factor receptor α1, glial cell line-derived neutrophic factor receptor α2, growth related protein, growth related protein α, growth related protein β, growth related protein γ, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor α, nerve growth factor nerve growth factor receptor, neurotrophin-3, neurotrophin-4, placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor α, platelet derived growth factor receptor β, pre-B cell growth stimulating factor, stem cell factor receptor, TNF, including TNF0, TNF1, TNF2, transforming growth factor α, transforming growth factor β, transforming growth factor β1, transforming growth factor β1.2, transforming growth factor β2, transforming growth factor β3, transforming growth factor β5, latent transforming growth factor β1, transforming growth factor β binding protein I, transforming growth factor β binding protein II, transforming growth factor β binding protein III, tumor necrosis factor receptor type I, tumor necrosis factor receptor type II, urokinase-type plasminogen activator receptor, vascular endothelial growth factor, and chimeric proteins and biologically or immunologically active fragments thereof.

Therapeutic moieties also include, in some embodiments, chemotherapeutic agents. A chemotherapeutic agent contemplated for use in a reagent of the disclosure includes, without limitation, alkylating agents including: nitrogen mustards, such as mechlor-ethamine, cyclophosphamide, ifosfamide, melphalan and chlorambucil; nitrosoureas, such as carmustine (BCNU), lomustine (CCNU), and semustine (methyl-CCNU); ethylenimines/methylmelamine such as thriethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil, fluorodeoxyuridine, gemcitabine, cytosine arabinoside (AraC, cytarabine), 5-azacytidine, 2,2'-difluorodeoxycytidine, purine analogs such as 6-mercaptopurine, 6-thioguanine, azathioprine, 2'-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; epipodophylotoxins such as etoposide and teniposide; antibiotics such as actimomycin D, daunomycin (rubidomycin), doxorubicin, mitoxantrone, idarubicin, bleomycins, plicamycin (mithramycin), mitomycinC, and actinomycin; enzymes such as L-asparaginase; biological response modifiers such as interferon-alpha, IL-2, G-CSF and GM-CSF; miscellaneous agents including platinium coordination complexes such as cisplatin and carboplatin, anthracenediones such as mitoxantrone, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide. Gefitinib and erlotinib are also specifically contemplated.

Dosages of the therapeutic moiety provided are administered as a dose measured in, for example, mg/kg. Contemplated mg/kg doses of the disclosed therapeutics include about 1 mg/kg to about 60 mg/kg. Specific ranges of doses in mg/kg include about 1 mg/kg to about 20 mg/kg, about 5 mg/kg to about 20 mg/kg, about 10 mg/kg to about 20 mg/kg, about 25 mg/kg to about 50 mg/kg, and about 30 mg/kg to about 60 mg/kg. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

"Effective amount" as used herein refers to an amount of a reagent of the disclosure sufficient to visualize the identified disease or condition, or to exhibit a detectable therapeutic or inhibitory effect. The effect is detected by, for example, an improvement in clinical condition or reduction in symptoms. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

Visualization of Reagents

Visualization of binding to dysplastic cells or cancerous cells is by any means known to those of ordinary skill in the art. As discussed herein, visualization is, for example and without limitation, in vivo, in vitro, or in situ visualization.

In some embodiments where the detectable label is a radiolabel, the radiolabel is detected by nuclear imaging. Nuclear imaging is understood in the art to be a method of producing images by detecting radiation from different parts of the body after a radioactive tracer material is administered. The images are recorded on computer and on film.

Some embodiments of methods of the disclosure involve the acquisition of a tissue sample from a patient. The tissue sample is selected from the group consisting of a tissue or organ of said patient.

Formulations

Compositions of the disclosure are formulated with pharmaceutically acceptable excipients such as carriers, solvents, stabilizers, adjuvants, diluents, etc., depending upon the particular mode of administration and dosage form. The compositions are generally formulated to achieve a physiologically compatible pH, and range from a pH of about 3 to a pH of about 11, about pH 3 to about pH 7, depending on the formulation and route of administration. In alternative embodiments, the pH is adjusted to a range from about pH 5.0 to about pH 8. In various aspects, the compositions comprise a therapeutically effective amount of at least one compound as described herein, together with one or more pharmaceutically acceptable excipients. Optionally, the compositions comprises a combination of the compounds described herein, or may include a second active ingredient useful in the treatment or prevention of bacterial growth (for example and without limitation, anti-bacterial or anti-microbial agents), or may include a combination of reagents of the disclosure.

Suitable excipients include, for example, carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants (for example and without limitation, ascorbic acid), chelating agents (for example and without limitation, EDTA), carbohydrates (for example and without limitation, dextrin, hydroxyalkylcellulose, and hydroxyalkylmethylcellulose), stearic acid, liquids (for example and without limitation, oils, water, saline, glycerol and ethanol) wetting or emulsifying agents, pH buffering substances, and the like.

EXAMPLES

The invention will be more fully understood by reference to the following examples which detail exemplary embodiments of the invention.

Materials and Methods Used in the Examples

Cells, Chemicals, and Materials

Human HT29, SW480, Q-hTERT, and SKBR3 cells were obtained from the American Type Culture Collection (ATCC, Manassas, Va.). We used McCoy's Medium for HT29 and SKBR3, Dulbecco's Modified Eagle Medium (DMEM) for SW480, and Keratinocyte-SFM media (Gibco) for Q-hTERT. Flo-1 Her2 cells were maintained in DMEM supplemented with G418. All cells were cultured at 37° C. in 5% CO2, and were supplemented with 10% fetal bovine serum (FBS) with 1% penicillin/streptomycin. Penicillin/streptomycin was omitted for the siRNA knockdown studies. FBS was omitted for Keratinocyte-SFM media. The cells were passaged using 0.25% EDTA containing trypsin (Mediatech Inc, Mansas, Va.). The cell number was counted with a hemocytometer. Peptide synthesis reagents were obtained from either Anaspec (Fremont, Calif.) or AAPPTEC (Louisville, Ky.) and were of the highest grade available (>99% purity) and used without further purification. Solvents and other chemical reagents were purchased from Sigma-Aldrich (St. Louis, Mo.), unless otherwise mentioned.

Peptide Selection Using Structural Model

The crystal structure (ID #2A91) for HER2 extracellular domain (ECD) was obtained from the Protein Data Bank (PDB).83 A peptide library with 7 random amino acid residues was aligned with 2A91 using PepSite-2.40 ~1000 peptide sequences were generated using mimotopes. 36 We evaluated binding of candidate peptide sequences with the 2A91 protein structure specified by chain A. The software comprehensively evaluated all possible combinations of predicted binding motifs for each of the 7 amino acids, and generated a 3D model of the binding interactions between the candidate peptides and the HER2-ECD target. For each peptide, the raw score was fitted to a Gumbel distribution and then ordered by P-value.

Flo-1-Her2 and Q-hTERT cells were seeded with ~7,500 cells in 12-well plates with 1.5 mm thick glass cover slides, and grown to ~70% confluence. The cells were gently washed with cold PBS before adding the peptide. 10 µM of FITC-labeled peptide was added to each well and incubated at 4° C. for 1 hour. After incubation, the cells were washed 3× with PBS, fixed in ice-cold 4% PFA for 10 min, and washed 1× with PBS. Subsequently, the cells were embedded on microscope slides with ProLong Gold reagent containing DAPI (Invitrogen), and the slides where analyzed with a Leica TCS SP5 confocal microscope using 63× oil immersion objective (Leica Microsystems, Leider Lane IL). The FITC-labeled peptides and anti-HER2 antibody were tested in quadruplicate.

Peptide Synthesis

We synthesized and labeled the peptides with either FITC or Cy5.5-using standard Fmoc-mediated solid-phase chemical synthesis. We used Fmoc and Boc protected L-amino acids, and synthesis was assembled on rink amide MBHA resin. The peptides were synthesized on a PS3 automatic synthesizer (Protein Technologies Inc. Tucson, Ariz.). The C-terminus lysine was incorporated as Fmoc-Lys (ivDde)-OH, and the N-terminus amino acid was incorporated with Boc protection to avoid unwanted Fmoc removal during deprotection of the ivDde moiety prior to fluorophore labeling. Upon complete assembly of the peptide, the resin was transferred to a reaction vessel for manual labeling with dye. The ivDde side chain protecting group was removed with 5% hydrazine in DMF (3×20 min) with continuous shaking at room temperature (RT). The resin was washed with DiMethylFormamide (DMF) and DiChloroMethane (DCM) 3× each for 1 min. The protected resin-bound peptide was incubated overnight with either FITC or Cy5.5-NHS ester (Lumiprobe LLC, Hallandale Beach, Fla.) in the presence of DIEA, and the completion of the reaction was monitored by a qualitative Ninhydrin test. Upon completion of labeling, the peptide was cleaved from the resin using TFA:TIS:H2O (95:2.5:2.5 v/v/v) for 4 hours with shaking in the dark at RT. After separating the peptide from the resin, the filtrate was evaporated with N2 gas followed by precipitation with chilled diethyl ether and stored overnight at −20° C. The precipitate was centrifuged at 3000 rpm for 5 min and washed with diethyl ether 3× and centrifuged in between each washing step. The crude peptides were dissolved in 1:1 acetonitrile/H2O (v/v) and purified by prep-HPLC with a C18 column (Waters Inc, Milford, Mass.) using a water (0.1% TFA)-acetonitrile (0.1% TFA) gradient. The final purity of the peptides was confirmed by analytical C18-column. Further characterization was performed with either ESI (Waters Inc.) or Q-TOF (Agilent Technologies) mass spectrometry. The scrambled (control) peptide PPS*-Cy5.5 was synthesized, labeled and purified using the same method.

Spectral Measurements

The peptide absorbance spectra were collected using a NanoDrop 2000 spectrophotometer (Thermo Scientific, Waltham, Mass.). The fluorescence emission with collected with a fiber coupled spectrophotometer (Ocean Optics, Dundin, Fla.), using a diode-pumped solid state laser (Technica Laser Inc, Winter Park, Fla.) with $\lambda_{ex}$=671 nm. The spectrophotometer probe was placed in contact with a 5 µM peptide solution diluted in PBS. Spectra was plotted using Origin 6.1 software (OriginLab Corp, Northampton, Mass.).

Confocal Fluorescence Microscopy

Cells were washed with PBS and incubated with 5 µM of KSP*-Cy5.5 and PPS*-Cy5.5 for 30 min at 4° C. The cells were then washed 3× in PBS, fixed with ice cold 4% paraformaldehyde (PFA) for 10 min, washed 1× with PBS, and then mounted on glass slides with ProLong Gold reagent containing DAPI (Invitrogen). Confocal fluorescence images were collected with Cy5.5, and DAPI filters (Leica Inverted SPSX Confocal Microscope System). For antibody staining, the cells were pre-fixed with cold methanol for 10 min at −20° C. and blocked with 2% BSA for 30 min at RT. Cells were incubated with 1:450 dilution of anti HER2 antibody overnight at 4° C. The cells were washed 3× with PBS and processed for secondary staining. Goat-anti rabbit Alexa-Fluor 488 (AF488) was added to the cells and incubated for 1 hour at RT. Cells were further washed 3× with PBS and mounted onto glass cover slips. Fluorescence intensities from 3 independent images were quantified using custom Matlab (Mathworks) software.

siRNA Knockdown of HER2 and Co-Localization

We examined knockdown of HER2 in HT29 cells using ON-TARGETplus human ERBB2 siRNA (# L-003126-00-0005), ON-TARGETplus Non-targeting pool (# D-001810-10-05), and DharmaFECT transfection reagents from Thermo Scientific (Waltham, Mass.). Briefly, cells were seeded in 6-well culture plates at 30% confluence in McCoy's 5A medium supplemented with 10% fetal bovine serum without antibiotics. The next day, cells were transfected with siRNA at a final concentration of 5 μmol/L using oligofectamine (Thermo Scientific). Knockdown of HER2 was confirmed by western blot. Cells were first washed in PBS and then lysed in RIPA buffer containing 1% Nonidet P40, 0.5% sodium deoxycholate, 0.1% SDS, 10 mg/ml phenylmethylsulfonylfluoride, and 1 mM sodium orthovanadate. Aliquots were placed on ice for 30 min and centrifuged at 14,000 RPM for 10 min. Protein aliquots were denatured in loading buffer at 95° C. for 5 min, separated on SDS-polyacrylamide gels (SDS-PAGE), and transferred onto PVDF membranes. The membrane was blocked with blocking buffer (5% skim milk in 0.1% PBST) for 30 min. The membranes were incubated with anti-HER2 primary antibody at 4° C. overnight. After washing 5× with PBST and 5× with PBS, the membrane was incubated for 1 hour in peroxidase-conjugated secondary antibody (1:5000 dilution; GE Healthcare, UK), and were developed using the western blot chemiluminescent substrate (GE Healthcare, USA). The luminescent signal was detected by exposure to X-ray film (Denville Scientific; NJ, USA).

We evaluated co-localization of binding by KSP*-Cy5.5 and validated anti-HER2 antibody to the surface of HT29 cells. KSP*-Cy5.5 at 5 μM concentration was incubated for 1 hour at 4° C. The cells were washed and fixed with 4% PFA for 5 min, and then incubated with primary anti-HER2 and secondary AF488-labeled antibody. We administered the peptide reagent first because of its lower affinity. The lower concentration (<10 μM) is less likely to interfere with antibody binding.

Competition for Peptide Reagent Binding

Specific binding of KSP*-Cy5.5 to HT29 cells was validated on competitive inhibition with unlabeled KSP* peptide reagent. ~7500 HT29 cells were grown to ~70% confluence on cover slips in triplicate. Unlabeled KSP* peptide at 0, 10, 25, 50, and 100 μM were added and incubated with the cells for 30 min at 4° C. The cells were washed 3× with PBS, and further incubated with 2 μM of KSP*-Cy5.5 for another 30 min at 4° C. The cells were washed 3× with PBS and fixed with 4% PFA for 10 min. The cells were washed with PBS and mounted with ProLong Gold reagent containing DAPI (Invitrogen). Confocal fluorescence images were collected at each concentration, and intensities from 3 independent images were quantified using custom Matlab (Mathworks) software.

Measurement of Peptide Reagent Binding Affinity and Time Constant

We measured the apparent dissociation constant of the HER2 peptide reagent to HT29 cells as an assessment of binding affinity. KSP*-Cy5.5 was serially diluted in PBS at concentrations of 0, 5, 10, 25, 50, 100, and 200 nM. ~105 HT29 cells were incubated with KSP*-Cy5.5 at 4° C. for 1 hour and washed with cold PBS. The mean fluorescence intensities were measured with flow cytometry (BD® LSRII, BD Biosciences). The equilibrium dissociation constant $k_d=1/k_a$ was calculated by performing a least squares fit of the data to the non-linear equation I, $(I0+Imaxka[X])/(I0=ka[X])$. I0 and Imax are the initial and maximum fluorescence intensities, corresponding to no peptide reagent and at saturation, respectively, and [X] represents the concentration of the bound peptide reagent. Graphpad prism analysis software (Graphpad Software Inc, La Jolla, Calif.) was used to calculate kd and ka.

We measured the apparent association time constant of the peptide reagent to HT29 cells to assess timing of binding. HT29 cells were grown to ~80% confluence in 10 cm dishes, and detached with PBS-based cell dissociation buffer (Invitrogen). ~105 cells were incubated with 5 μM KSP*-Cy5.5 at 4° C. for various time intervals ranging from 0 to 60 min. The cells were centrifuged, washed with cold PBS, and fixed with 4% PFA. Flow cytometry was performed, and the median fluorescence intensity (y) was ratioed with that of HT29 cells without addition of peptide reagent at different time points (t) using Flowjo software. The rate constant k was calculated by fitting the data to a first order kinetics model, $y(t)=Imax[1-exp(-kt)]$, where Imax=maximum value, 82 using Graphpad Prism 5.0 software.

Effect of HER2 Peptide on Cell Signaling

SKBR3 cells are commonly used to evaluate HER2 signaling, and were grown in 6 well plates to ~60% confluence. Unlabeled KSP* peptide was added to separate wells at concentrations of 5 and 100 μM. Lapatinib, a tyrosine kinase inhibitor, was used as a positive control and was added in concentrations of 1, 25, 100 and 1000 nM. Lapatinib stock solution starting at 1 mg/mL was diluted in DMSO and PBS. 1% DMSO treated cells and untreated cells were used as control. After 48 hours following treatment, the cells were harvested for western blot analysis. Anti-HER2 antibody (Cell Signaling, #2165), phospho-HER2/ErbB2 (Tyr1248) antibody (Cell Signaling, #2247), anti-AKT (Cell Signaling, #4691P), anti-ERK1/2 (Cell Signaling, #4695P), anti-phospho-AKT (pS473), (Cell Signaling, #4060P), anti-phospho-ERK1/2 (Cell Signaling, #4370P) and anti-tubulin (Invitrogen, #32-2600) were used per manufacturer's instructions.

In Vivo Imaging of Topical HER2 Over Expressed in Mouse Colonic Neoplasia

Mouse imaging studies were performed with approval of the University of Michigan Committee on the Use and Care of Animals (UCUCA). The mice were housed in pathogen-free conditions and supplied water ad libitum under controlled conditions of humidity (50±10%), light (12/12 hour light/dark cycle) and temperature (25° C.). Anesthesia was induced and maintained via a nose cone with inhaled isoflurane mixed with oxygen at a concentration of 2-4% at a flow rate of ~0.5 L/min. The colon was first rinsed with tap water to remove mucous and debris. White light illumination was used first to identify anatomic landmarks, including polyps, mucosal folds, colonic segment, and distance of endoscope tip from anus, to register the in vivo images with histology. The Cy5.5-labeled peptide reagents were locally delivered at a concentration of 100 μM in a volume of 1.5 mL through the 3 Fr instrument channel. After 5 min for incubation, the colon was rinsed 3× with a tap water to remove the unbound peptide reagents. Imaging was performed using a small animal endoscope (Karl Storz Veterinary Endoscopy). During imaging, we recorded the 1) distance between the endoscope tip and the anus and 2) clockwise location of each region of high intensity. Several days later, endoscopy was repeated to confirm that all residual signal from KSP*-Cy5.5 had disappeared, and then the mice were imaged with the PPS*-Cy5.5 control peptide reagent.

White light and fluorescence videos were exported in avi format with 24 (RGB) and 8 (grayscale) bit digital resolution for the color and fluorescence images, respectively. Streams that showed minimum motion artifact and absence of debris (stool, mucus) were selected for quantification. Individual frames were exported using custom Matlab software. On the fluorescence images, 3 regions of interest (ROI) with dimensions of 25×25 pixels were picked to represent a range of staining for normal and diseased tissues and averaged. The mean intensities within these ROI were determined to calculate the target to-background (T/B) ratio.

In Vivo Imaging of Intravenous HER2 Over Expressed in Mouse Colonic Neoplasia

Mice were anaesthetized using isoflurane, administered 200 µL of KSP*-Cy5.5 peptide reagent at 300 µM concentration via the tail vein. The imaging was performed prior to peptide reagent injection to assess baseline fluorescence and after injection until the maximum signal was observed. The ratio of fluorescence intensity in the adenoma to that in the normal region was calculated by drawing regions of interest at each time point Ex Vivo Macroscopic Validation of HER2 Over Expressed in Mouse Colonic Neoplasia After imaging, the colon was excised, flushed with PBS, and opened longitudinally for imaging with the IVIS 200 system using a Cy5.5 filter (Caliper Life Sciences, Hopkinton, Mass.). NIR fluorescence images were collected using 675 nm excitation and 720 nm emission with 1 sec exposure. A ruler was placed next to the specimen to determine the distance from the anus for registration with the endoscopy and histology images. The specimen was then processed for histology by cutting sections in the plane parallel to the mucosal surface. Digital images were collected with a Zeiss Axiovision microscope (Thornwood, N.Y.) using 5× magnification, and stitched together using Image Composite Editor (Microsoft, Redmond, Wash.). An expert gastrointestinal pathologist (SRO) who was blinded to the imaging results reviewed the histology, and identified regions of dysplasia and normal colon. Fluorescence intensities from these sites were measured from two concentric ellipses of equal area from the normal and polyp using Living Image 4.0 software (Caliper Life Sciences; Hopkinton, Mass.). The intensities from the polyp and normal were used to define the target (T) and background (B) values, respectively.

Peptide Reagent Immunofluorescence on Mouse Colonic Adenomas

Specimens of mouse colonic adenoma were formalin fixed and processed, as described previously. Serial 5 µm sections were incubated with 2 µM of each peptide for 10 min at RT. The sections were washed 3× with PBS, and mounted with Prolong Gold reagent containing DAPI (Invitrogen). Adjacent sections were processed for histology (H&E).

Binding of HER2 Peptide Reagent to Human Proximal Colonic Neoplasia

Formalin-fixed, paraffin-embedded (FFPE) specimens of human proximal colon were obtained from the archived tissue bank in the Department of Pathology. 5 µm thick sections were cut, and mounted onto glass slides (Superfrost Plus, Fischer Scientific). The tissues were deparaffinized, and antigen retrieval was performed. The sections were blocked with protein serum for 15 min at RT followed by rinsing with PBS. The sections were then stained with KSP*-Cy5.5 at 5 µM concentration for 10 min at RT. The sections were then washed 3× with PBS (3 min each) and further incubated with anti-HER2 antibody overnight at 4° C. Sections were washed 3× with PBST and mounted with Prolong Gold reagent containing DAPI (Invitrogen) using #1 cover glass (1.5 µm thickness). We placed 3 boxes with dimensions of 20×20 µm2 completely within colonic epithelium in each image, and measured the mean fluorescence intensities using custom Matlab software. Regions of saturated intensities were avoided.

Over Expression of HER2 in Human Proximal Colon

Immunohistochemistry (IHC) was performed using 1:450 dilution of anti-HER2/neu (#29D8; rabbit monoclonal antibody #2165) from Cell Signaling Inc (Danvers, Mass.). Vectastain Elite kit (Vector Laboratories Inc, Burlingame, Calif.) was used per manufacturer's instructions. Briefly, formalin-fixed specimens were deparaffinized using a standard dehydration/rehydration protocol and antigen unmasking was performed by boiling the slides in 10 mM sodium citrate buffer with 0.05% Tween at pH 6.0, and then maintaining at a sub-boiling temp for 15 min. The slides were cooled for 30 min. The sections were washed 3× with dH2O for 3 min, and then incubated in 3% H2O2 in methanol for 10 min. The sections were washed 3× in dH2O for 2 min and in PBST for 5 min. Blocking was performed with protein blocking agent # X0909 from Dako (Carpinteria, Calif.) for 15 min at RT. The blocking solution was washed 1× with PBS. The sections were incubated with anti-HER2/neu antibody overnight at 4° C. in a humidified chamber and then washed 3× in PBST for 5 min. A 1:200 dilution of biotinylated secondary antibody (goat anti-rabbit IgG) was added to each section and incubated for 30 min at RT, and then removed by washing 3× with PBST for 5 min. Premixed Elite Vectastain ABC reagent from Vector Labs was added to each section and incubated for 30 min at RT. The sections were washed 3× in PBS for 5 min, and developed with 3,3'-diaminobenzidine (DAB) substrate. The reaction was monitored for up to 5 min, and then quenched by immersing the slides in dH2O. Hematoxylin was added as a counterstain for ~20 sec, and the sections were dehydrated in increasing concentrations of ethyl alcohol (2× each at 70%, 80%, 95%, and 100%). Coverslips were mounted using permount mounting medium (# SP15-100, Fisher) in xylene. Serial sections were processed for routine histology (H&E).

IHC scoring was performed independently by gastroenterology pathology experts without prior knowledge of clinicopathological information or molecular imaging results. The scoring was performed according to the DAKO HercepTest™ guidelines as follows: 0+, no reactivity or membrane staining in ≥10% of tumor cells; 1+, faint/barely perceptible partial membrane staining in ≥10% of tumor cells; 2+, weak-to-moderate complete or basolateral membrane staining in ≥10% of tumor cells; 3+, moderate-to-strong complete membrane staining in ≥10% of tumor cells. IHC scoring with 2+ and 3+ were considered to be positive for HER2 over expression.

Statistical Analysis

Fluorescence intensities were transformed in base-2 log if needed to improve normality and stabilize variance. The fold-change between classification pairs was estimated using the anti-log of the difference in the log-transformed data. We fit the human data with 4 histological classifications with a one-way ANOVA model and used Tukey's multiple comparisons. Co-localization of peptide reagent and antibody binding was evaluated on Pearson's correlation coefficient.

Example 1

Peptide Selection Using a Structural Model

We identified peptides that bind specifically to the extracellular domain (ECD) of HER2 (2A91) using a structural model, FIG. 1A [Garrett et al., Mol Cell. 11: 495-505 (2003)]. The ECD was targeted because it is accessible to imaging. We generated ~1000 candidates using mimotopes (www.mimotopes.com) by considering Arg or Lys amino acid residues at the N-terminus to form hydrophilic interactions with HER2-ECD [Lemmon, Exp. Cell Res., 315: 638-648 (2009); Franklin et al., Cancer Cell, 5: 317-328 (2009)]. Hydrophobic residues such as Phe, Trp, Val, Met, Ile, and Leu were appended at the C-terminus to increase the likelihood of hydrophobic/hydrophilic interaction (Garrett et al., supra). Other amino acids such as Ser, His, Arg, Tyr, Thr, Asp, and Asn were used to increase peptide diversity [Wang et al., Anal Chem. 18: 8367-8372 (2015)]. Either the N or C-terminus of the peptides was connected by a conformationally rigid spacer group, such as PFP, PNP, PYP, and PWP, in the middle region. We evaluated binding interactions of these candidates to HER2-ECD domain 1-3 using Pepsite-2 [Trabuco et al., Nucleic Acids Res., 40: W423-426 (2012)]. We synthesized the five leading candidates based on P-value.

KSPNPRF (SEQ ID NO: 1)

RHPFPRF (SEQ ID NO: 2)

RHPWPNR (SEQ ID NO: 3)

RHPYPQR (SEQ ID NO: 4)

RKPFPRH (SEQ ID NO: 5)

Figure 1B:
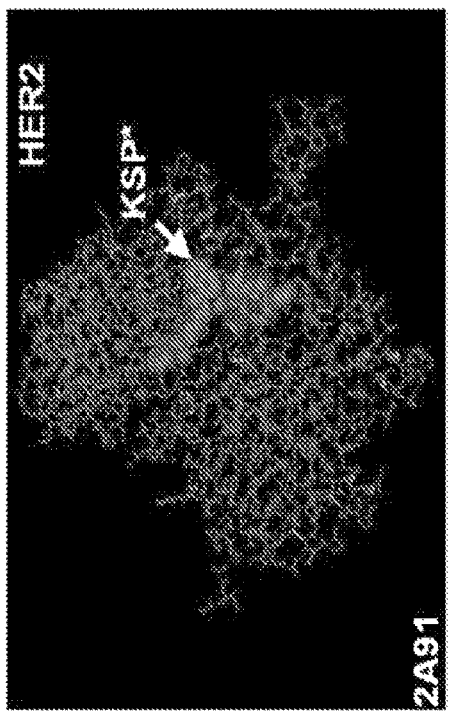
Figure 1C:
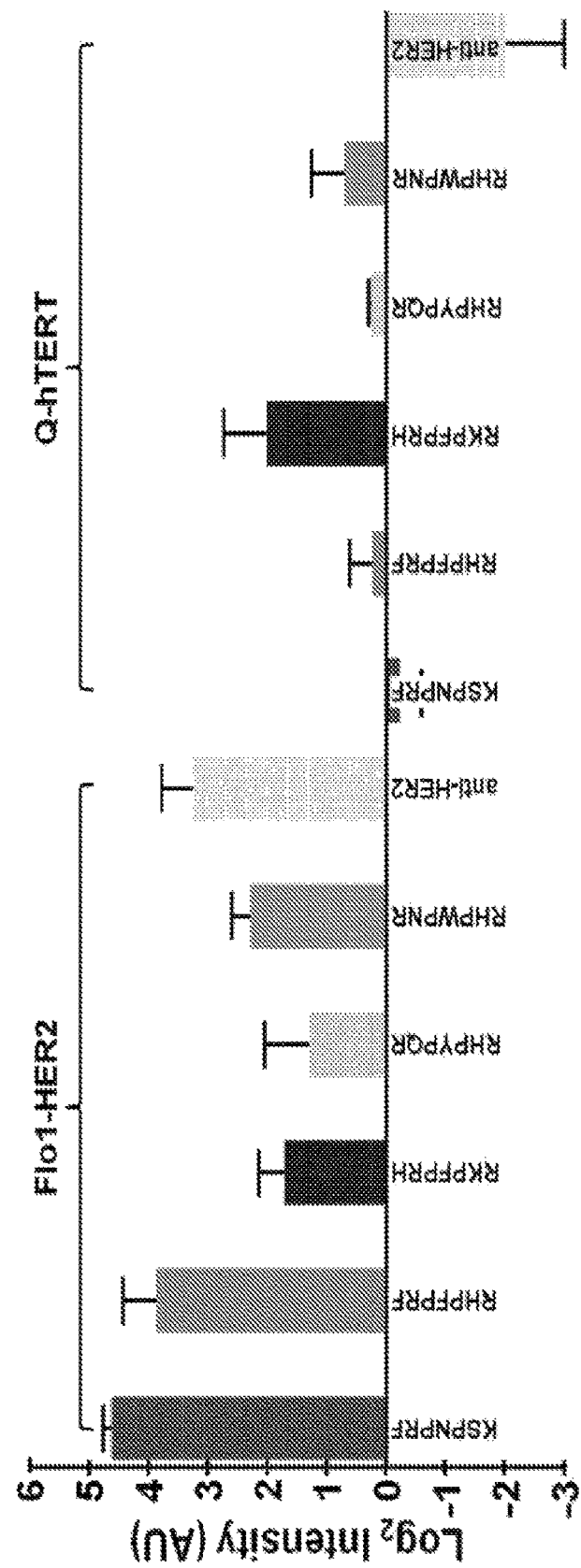
Figure 1D:
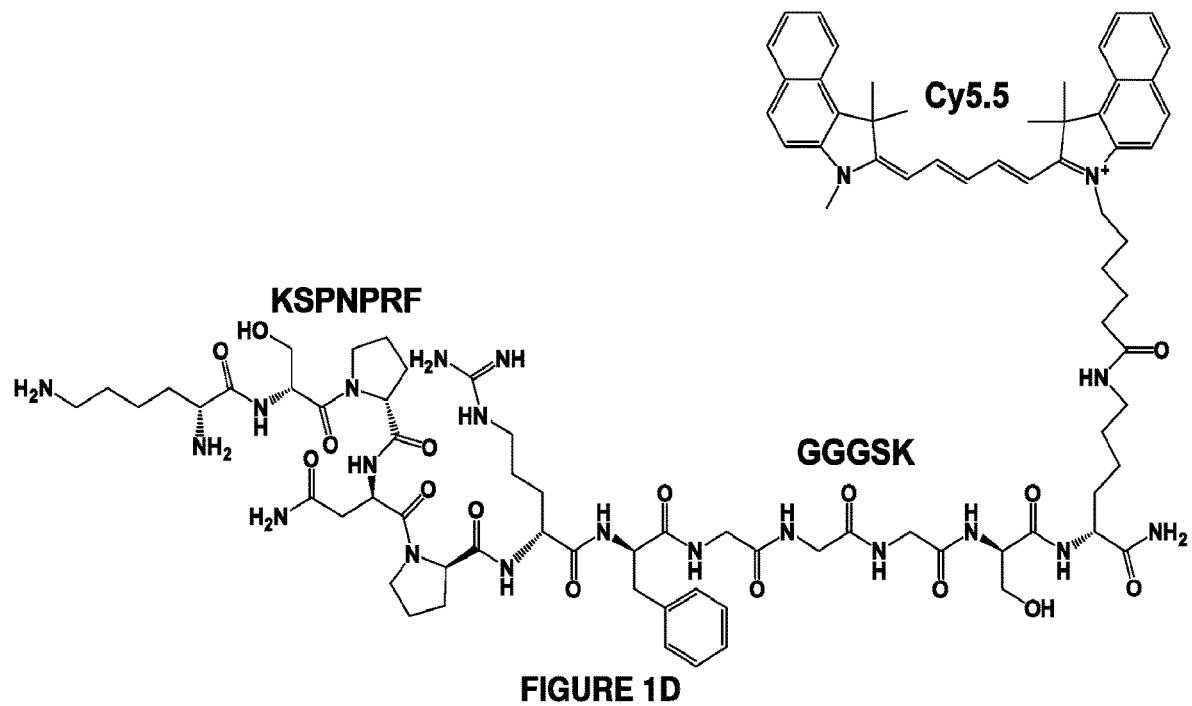
Figure 1E:
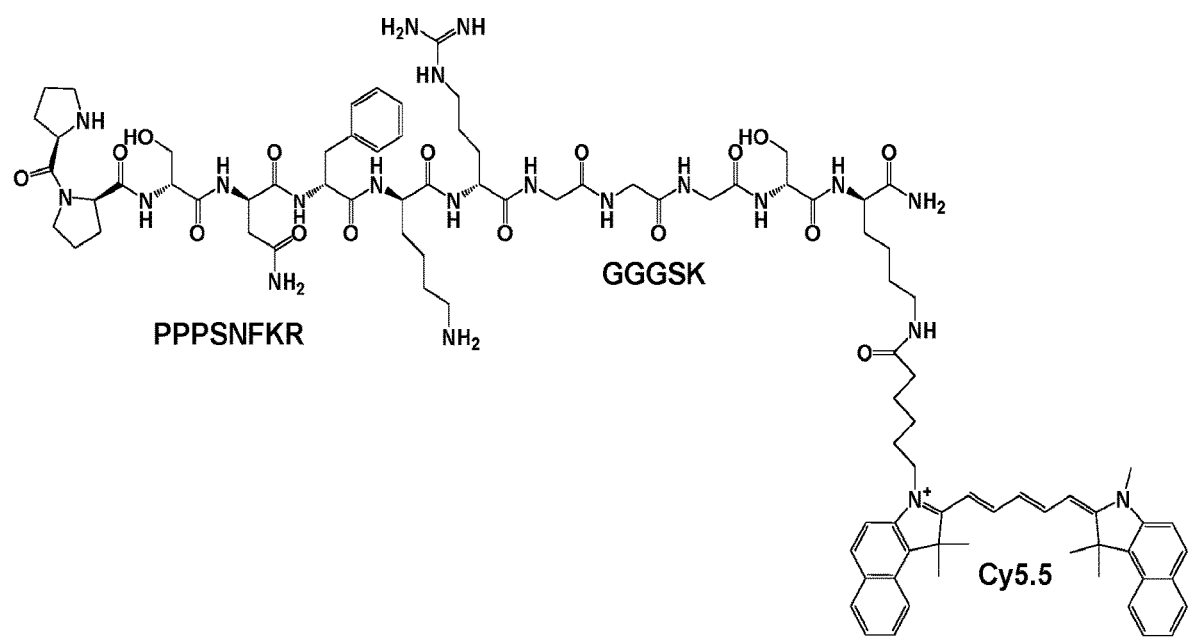
Figure 1F:
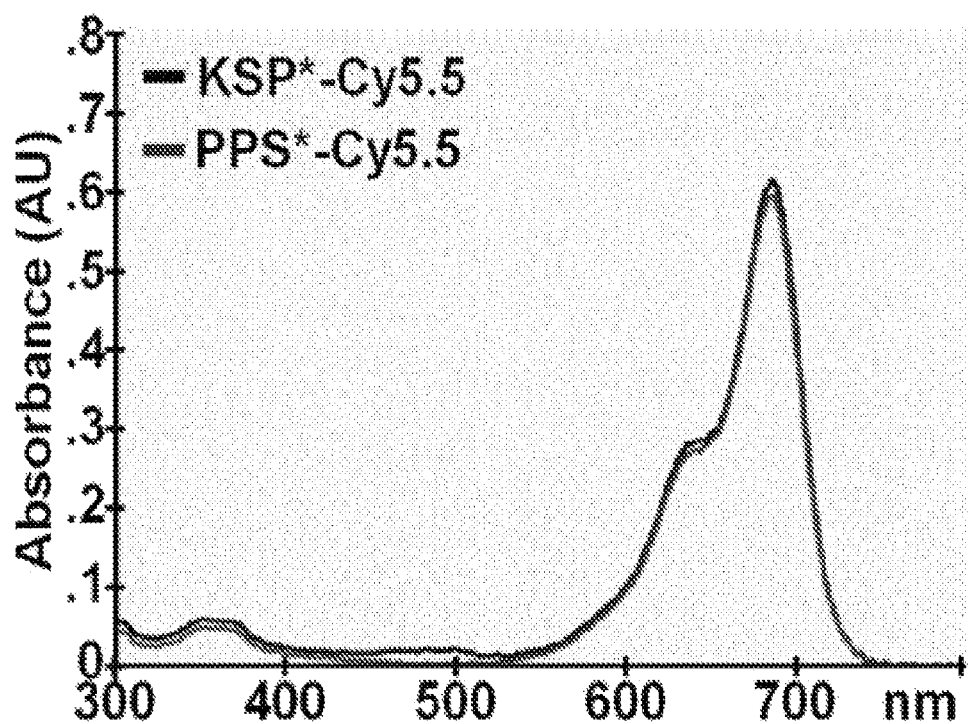
Figure 1G:
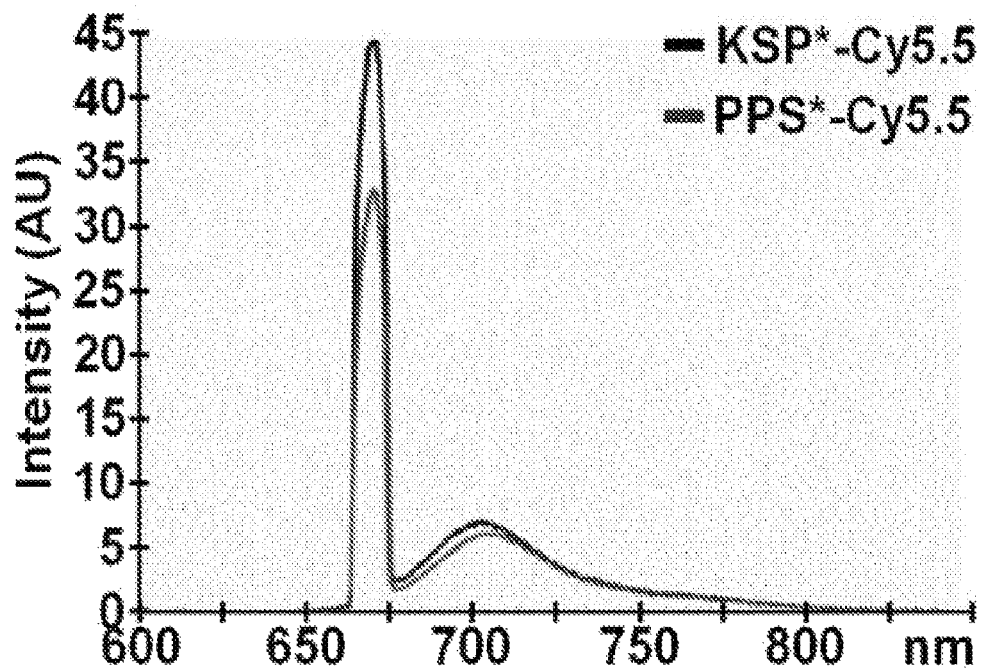

We attached a FITC label to each peptide, and imaged binding to Flo1-HER2 and Q-hTERT cells (control) using confocal microscopy. Western blot of these cells show difference in HER2 expression, FIG. 1B. We selected KSPNPRF based on the highest mean fluorescence intensity with binding to Flo1-HER2, FIG. 1C. From our model, this peptide binds to HER2 domain 3. The peptide (black) was then labeled for deep tissue imaging with a Cy5.5 (red) fluorophore via a GGGSK linker (blue) on the C-terminus, hereafter KSP*-Cy5.5, FIG. 1D. Cy5.5 was chosen for high quantum yield and photostability. The linker prevents steric hindrance by spatially separating the fluorophore from the peptide. We developed a scrambled sequence PPSNFKR for use as control by altering the conformationally rigid spacer PNP and moving both hydrophobic and hydrophilic amino acids at the C-terminus. We also linked this control peptide to Cy5.5 via GGGSK, hereafter PPS*-Cy5.5, FIG. 1E. The absorbance spectra of KSP*-Cy5.5 and PPS*-Cy5.5 at 5 µM in PBS shows a maximum at 680 nm, FIG. 1F. The fluorescence emission peak occurs at 708 nm in the NIR spectrum. For both peptides, we achieved >98% purity with HPLC, and measured an experimental mass-to-charge (m/z) ratio on mass spectrometry of 1794.98, which agrees with expected values, FIG. 8A,B.

Example 2

Confocal Fluorescence Microscopy

Figure 2G:
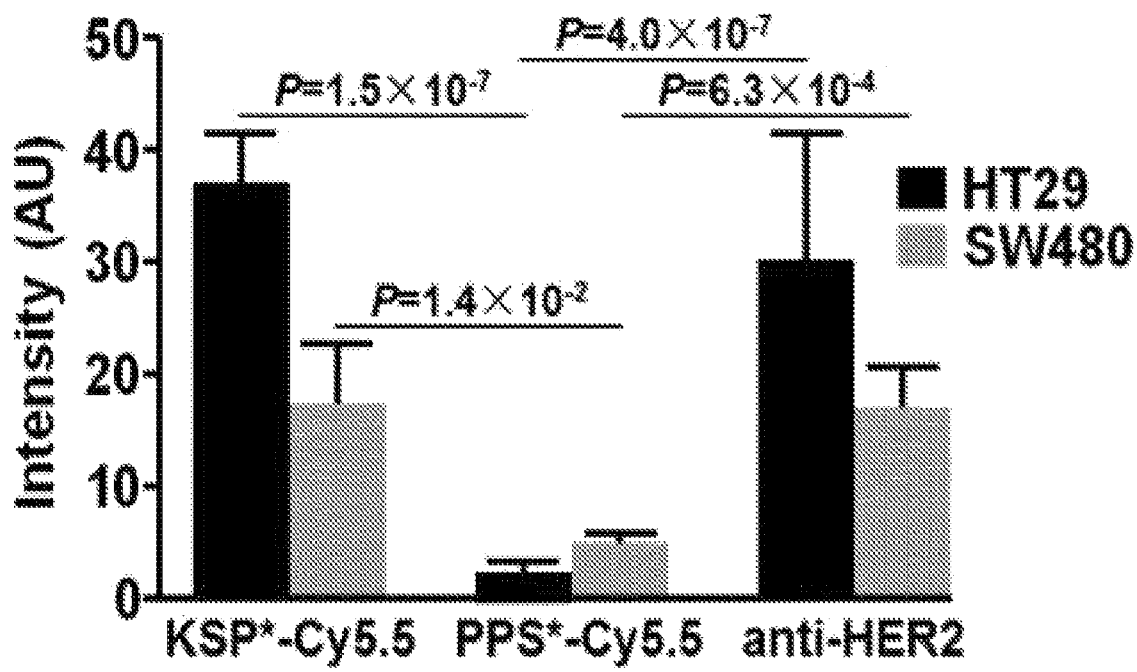
FIG. 2—Validation of specific peptide reagent binding to HER2 expressed on cell surface. On confocal microscopy, A,B) KSP*-Cy5.5 (red) binds to the surface (arrows) of HT29 and SW480 cells, while C,D) PPS*-Cy5.5 (negative control) shows minimal binding. E,F) Anti-HER2-AF488 (green) is used as a positive control. The mean fluorescence intensity for KSP*-Cy5.5 was significantly greater than that for PPS*-Cy5.5 for both HT29 and SW480 cells, P=1.5×$10^{-7}$ and 1.4×$10^{-2}$, respectively, by paired t-test. Similarly, the results for anti-HER2-AF488 were greater than that for PPS*-Cy5.5, P=4.0×$10^{-7}$ and 6.3×$10^{-4}$, respectively, by paired t-test. G) Each result is an average of 3 images collected independently. H) Western blot shows differences in HER2 expression between HT29 and SW480 cells. I,J) KSP*-Cy5.5 (red) and anti-HER2-AF488 (green) binds significantly greater to the surface (arrows) of siCL treated control HT29 cells compared to K,L) siHER2 knockdown cells, P=1.0×$10^{-4}$ and 1.7×$10^{-4}$, respectively, by paired t-test. M) Results are an average of 3 images collected independently. N) Western blot shows effective knockdown of HER2 (siHER2) compared to control (siCL). O) Binding of KSP*-Cy5.5 and anti-HER2-AF488 co-localizes to surface of HT29 cells, Pearson's coefficient ρ=0.74. P) On competition, we found the fluorescence intensities to decrease in a concentration dependent manner, P-values for intensity at each time point compared to that at 0 min are shown above data points. Each result is an average of 3 independent measurements. We measured Q) an apparent dissociation constant (binding affinity) of $k_d$=21 nM, $R^2$=0.98 for KSP*-Cy5.5 to HT29 cells, and an R) apparent association time constant k=0.14 $min^{-1}$ (7.1 min), $R^2$=0.92. Results for each measurement are representative of 3 independent experiments.
Figure 2H:
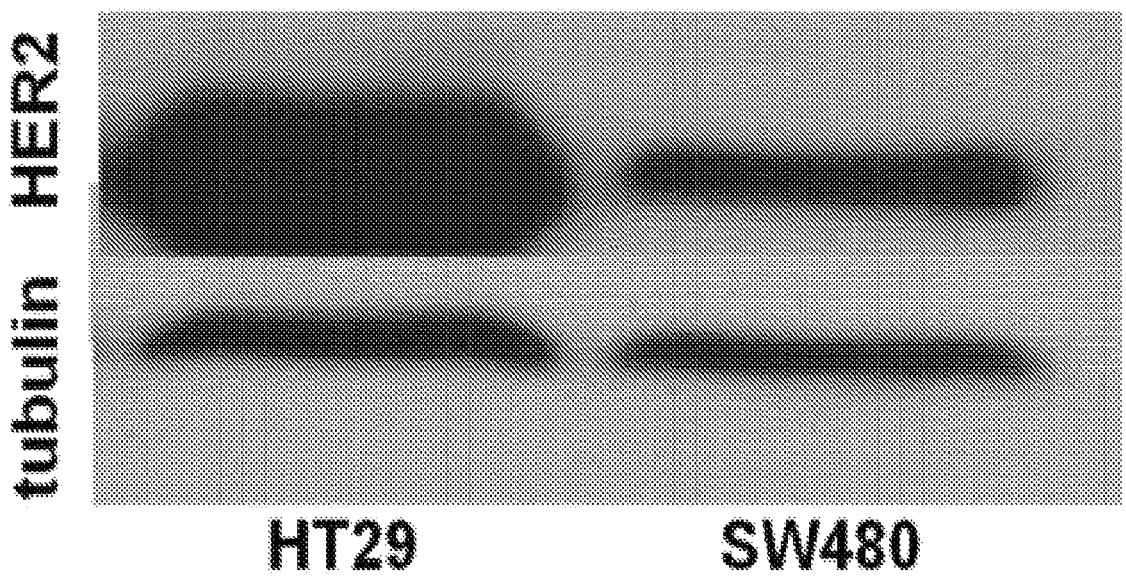

We performed confocal microscopy to demonstrate peptide binding to the plasma membrane (arrows), and observed significantly greater fluorescence intensity for KSP*-Cy5.5 than PPS*-Cy5.5 to HT29 and SW480 cells, FIG. 2A-D. An AF488-labeled anti-HER2 antibody also showed significantly greater signal than the control peptide, FIG. 2E,F. The quantified values are shown, FIG. 2G. Western blot shows difference in expression of HER2 for HT29 and SW480, FIG. 2H.

Example 3 siRNA Knockdown of HER2 and Co-Localization

Figure 3G:
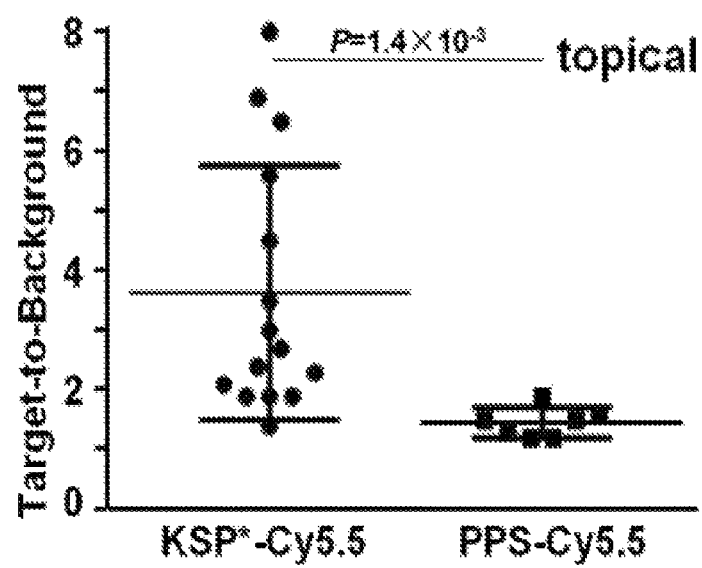
FIG. 3—In vivo imaging of mouse colonic dysplasia with topical HER2 peptide reagent. A) Endoscopic image with white light illumination shows a spontaneous polyp (arrow). B) NIR fluorescence image after topical administration of KSP*-Cy5.5 shows increased intensity from polyp (arrow). C) Image of same region with PPS*-Cy5.5 control several days later shows significantly reduced signal. D) White light and NIR fluorescence images with E) KSP*-Cy5.5 and F) PPS*-Cy5.5 show similar results with a flat adenoma (arrow). G) From n=7 mice, topically administered KSP*-Cy5.5 (n=15 adenomas) resulted in a higher mean (±std) T/B ratio than PPS*-Cy5.5 (n=7 adenomas), 3.64±2.13 and 1.46±0.25 respectively, P=1.4×$10^{-3}$ by unpaired t-test.

We performed siRNA knockdown experiments with HT29 cells to validate specific binding of KSP*-Cy5.5 to HER2. On confocal microscopy, KSP*-Cy5.5 (red) and AF488-labeled anti-HER2 antibody (green) bind strongly to the surface (arrow) of control HT29 cells (transfected with siCL, non-targeting siRNA), FIG. 2I,J. Significantly reduced fluorescence intensities were observed for HT29 knockdown cells (transfected with siHER2, targeting siRNA), FIG. 2K,L. Quantified results are shown, FIG. 3M. Western blot shows effective HER2 knockdown, FIG. 2N. Also, we observed co-localization of peptide reagent and antibody binding (arrow) on merged images (Pearson's coefficient $\rho=0.743$), FIG. 2O.

Example 4

Competition for Peptide Reagent Binding

Figure 2P:
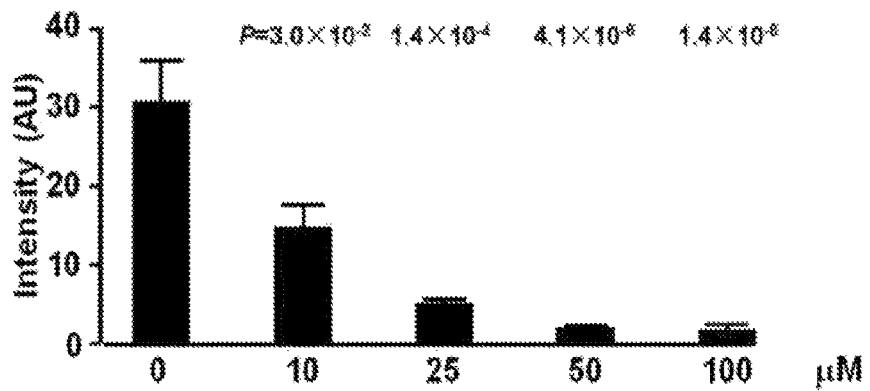

We performed competition studies to demonstrate that binding occurs with the peptide and not the fluorophore by adding unlabeled KSP* to compete with KSP*-Cy5.5 on HT29 cells. We found the fluorescence intensities to decrease significantly in a concentration dependent manner, FIG. 2P.

Example 5

Characterization of Peptide Reagent Binding

Figure 2Q:
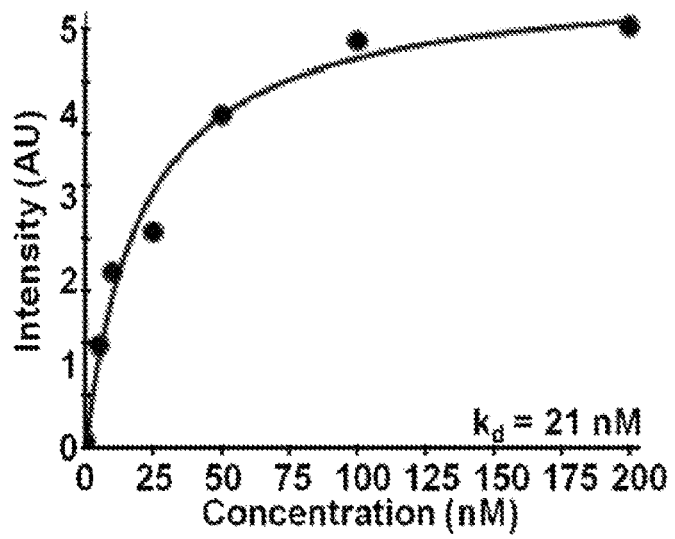
Figure 2R:
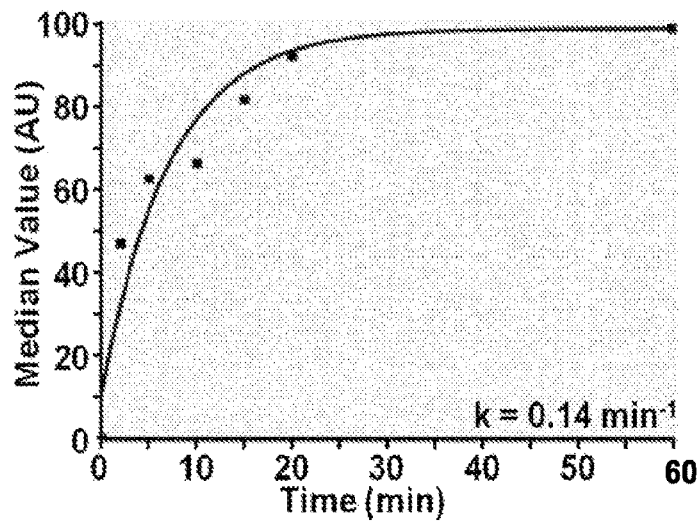

We evaluated the binding parameters of KSP*-Cy5.5 to HT29 cells using flow cytometry. We measured an apparent dissociation constant of kd=21 nM, R2=0.98, resulting in high binding affinity, FIG. 2Q. Also, we measured an apparent association time constant of k=0.14 min-1 (7.14 min), R2=0.92, to support rapid binding to topical administration, FIG. 2R.

Example 6

Effect of Peptide on Cell Signaling Pathways

Figure 9:
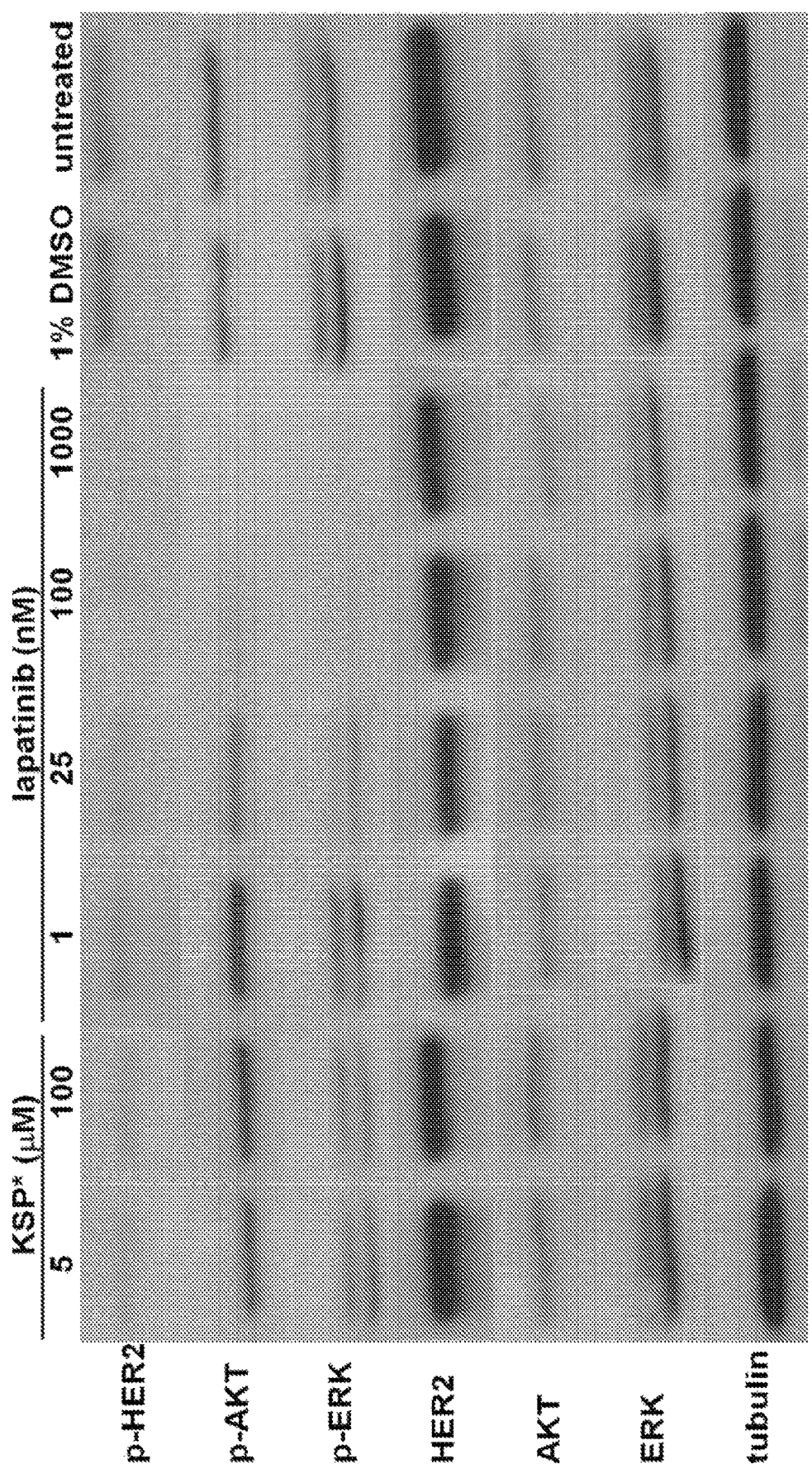
FIG. 9—HER2 peptide does not initiate cell signaling. HT29 cells incubated with KSP* showed no reduction in HER2 phosphorylation (p-HER2) and downstream phosphorylation of AKT and ERK at concentrations of 5 and 100 µM. By comparison, the same cells treated with lapatinib show a dose dependent reduction in p-HER2, p-AKT and p-ERK with increasing concentrations from 1 to 1000 nM. HT29 cells treated with 1% DMSO and untreated cells are show as control. β-tubulin is used as loading control.

We evaluated the effect of KSP* peptide binding on HER2-mediated signaling in SKBR3 cells. On western blot, we observed no change in phosphorylation of either HER2 (p-HER2) or of downstream AKT (p-AKT) and ERK (p-ERK) with addition of KSP* at 5 and 100 µM, FIG. 9. By comparison, the addition of lapatinib, a tyrosine kinase inhibitor known to interrupt HER2 signaling in solid tumors, showed reduced expression of p-HER2, p-AKT, and p-ERK in a concentration dependent manner. Cells treated with 1% DMSO treated and untreated cells showed no suppression of HER mediated signaling.

Example 7

In Vivo Imaging of HER2 Over Expressed in Mouse Colonic Neoplasia

We evaluated specific binding of KSP*-Cy5.5 to colonic adenomas that over express HER2 in CPC; Apc mice This mouse was genetically engineered to somatically delete an Apc allele under Cre regulation, and develops polypoid and flat adenomas spontaneously in the colon. This model is representative of human disease because Apc mutations are found in >80% of sporadic colorectal cancers. Imaging was performed in vivo using a small animal endoscope that is sensitive to NIR fluorescence. A white light image of a polypoid adenoma (arrow) was first identified, FIG. 3A.

KSP*-Cy5.5 was then topically administered, and allowed to incubate for several min. After the unbound peptide reagents were rinsed away, the fluorescence image shows increased intensity (arrow) at the polyp, FIG. 3B. After this signal disappeared several days later, images were then collected using PPS*-Cy5.5 (control) from the same area for comparison. Minimal signal was observed, FIG. 3C. Also, a flat adenoma (arrow) with subtle appearance on white light is shown, FIG. 3D. The corresponding fluorescence image shows increased intensity with visible crypt-like structures, FIG. 3E. Images collected several days later with PPS*-Cy5.5 show minimal signal, FIG. 3F. In all of the fluorescence images, surrounding normal colonic mucosa produced minimal background. Quantified results show significantly greater fluorescence intensity for dysplasia compared to normal, FIG. 3G.

Figure 4A:
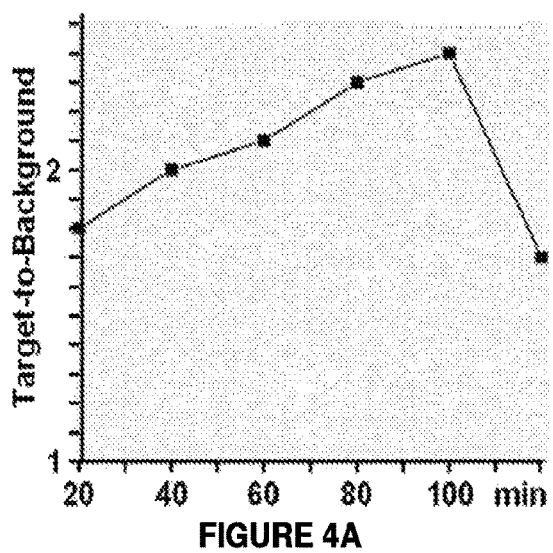
FIG. 4—In vivo imaging of mouse colonic dysplasia with systemic HER2 peptide reagent. A) With intravenous peptide reagent administration, the mean T/B ratio from colonic adenomas in n=4 mice shows a peak at 100 min. B) Representative fluorescence image from polyp shows region of increased intensity. C) The mean fluorescence intensity from adenomas was 5.03 fold higher than that from uninvolved surrounding normal mucosa, P=2.6×$10^{-9}$ by paired t-test. D) Representative white light image of exposed mucosal surface of excised mouse colon shows numerous polyps. E) Corresponding fluorescence image show increased fluorescence intensities at site of polyps.
Figure 4B:
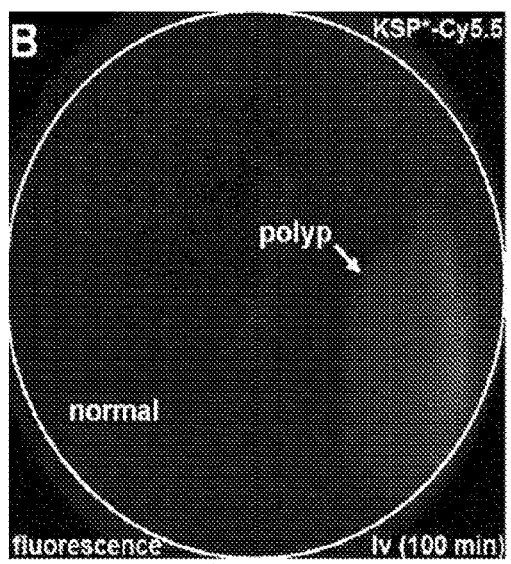

KSP*-Cy5.5 was then systemically administered via tail vein, and NIR fluorescence images were collected over time in each mouse. In n=4 mice, the mean intensity was found to peak at 100 min, FIG. 4A. A representative fluorescence image of a polypoid adenoma at 100 min after iv peptide reagent injection is shown, FIG. 4B.

Example 8

Figure 4C:
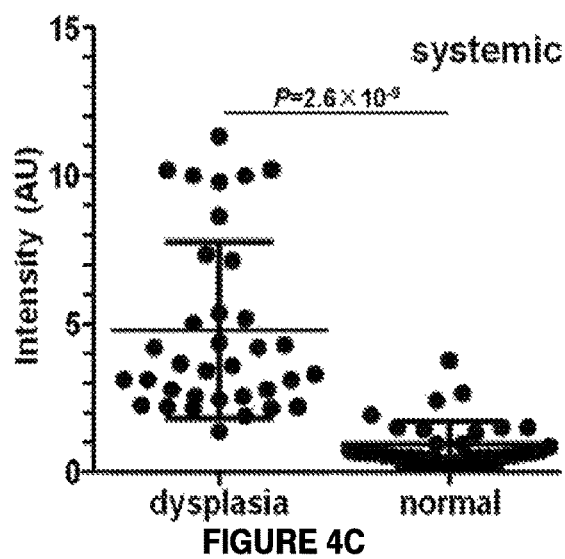
Figures 4D, 4E:
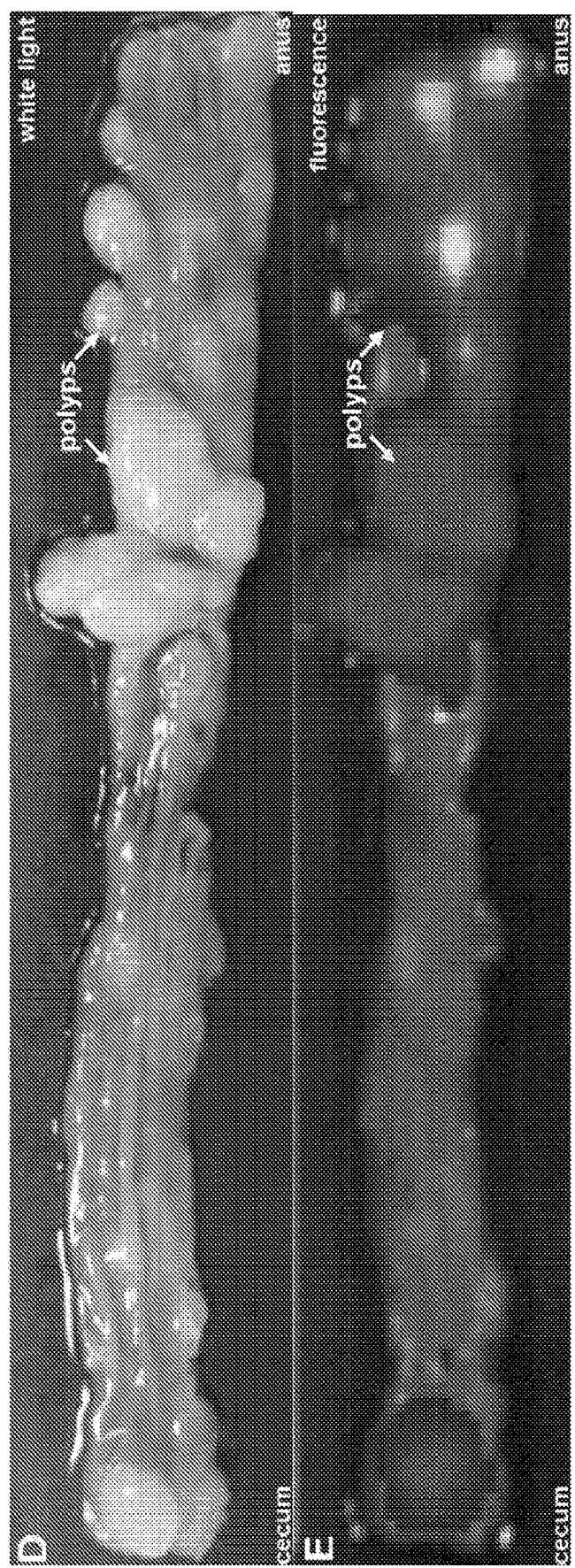

Ex Vivo Macroscopic Validation of HER2 Over Expressed in Mouse Colonic Neoplasia After imaging, the animals were euthanized, and the colon was excised and divided longitudinally to expose the mucosal surface for collection of macroscopic white light and fluorescence images with IVIS, FIG. 4D,E. The tissues were sectioned along planes parallel to the surface, and the pathologist (SRO) identified regions of dysplasia and normal on histology while blinded to the imaging results. In n=4 mice, we found significantly greater mean fluorescence intensities for dysplasia compared to normal, FIG. 4C.

We also sectioned the specimens for collection of confocal images to perform microscopic validation of peptide reagent binding. We found increased cell surface staining of KSP*-Cy5.5 compared with PPS*-Cy5.5 to dysplastic crypts (arrow), FIG. 5A,B. Minimal staining was observed for either peptide reagent with normal mouse colonic mucosa, FIG. 5D,E. Corresponding histology (H&E) is shown, FIG. 5C,F.

Figures 5G, 5H, 5I, 5J:
FIG. 5—Validation of specific peptide reagent binding to HER2 over expressed by mouse colonic dysplasia. On confocal microscopy, we found intense staining of A) KSP*-Cy5.5 compared to B) PPS*-Cy5.5 to sections of dysplasia. C) Histology (H&E) shows features of low-grade dysplasia (arrows). Minimal staining was observed with either D) KSP*-Cy5.5 or E) PPS*-Cy5.5. G) Histology (H&E). On immunohistochemistry with a known antibody, we confirmed over expression of HER2 in dysplasia. H) No antibody (control). Normal colonic mucosa I) with and J) without antibody (control).

We performed immunohistochemistry with a known antibody to validate over expression of HER2 in mouse colonic dysplasia, FIG. 5G. A serial section with no primary antibody used (control) showed minimal reactivity, FIG. 5H. By comparison, normal mouse colonic mucosa showed minimal reactivity either with or without anti-HER2, FIG. 5I,J.

Example 9

Binding of HER2 Peptide Reagent to Human Proximal Colonic Neoplasia

Figure 6I:
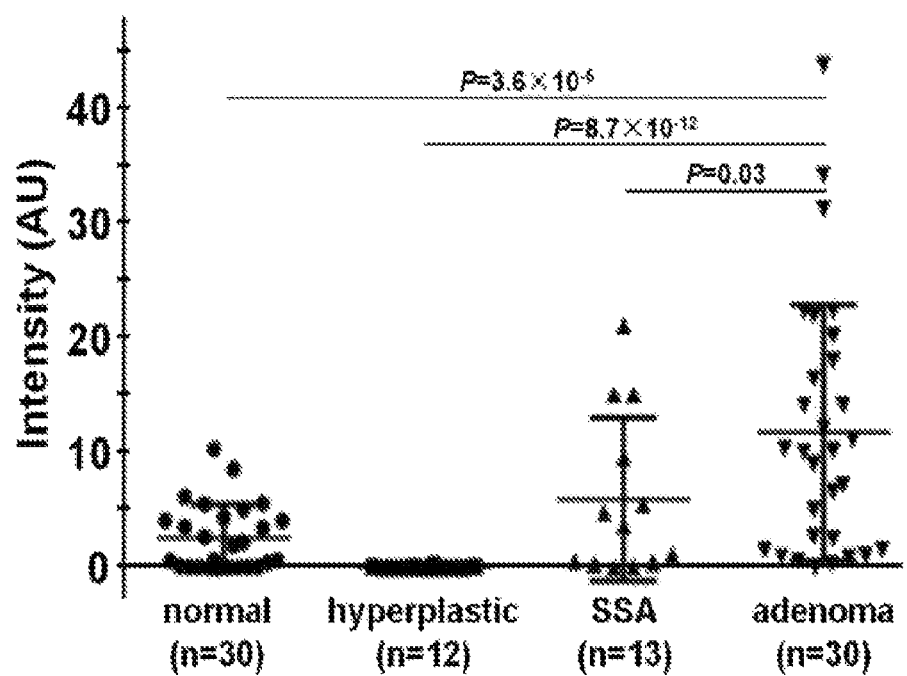
FIG. 6—Validation of specific peptide reagent binding to HER2 over expressed by human proximal colonic neoplasia. Increased fluorescence intensity was observed for staining of A) KSP*-Cy5.5 (red) and B) anti-HER2-AF488 antibody (green) to dysplasia (arrow). C) Corresponding histology (H&E) from adjacent section. D) Co-localization of peptide reagent (red) and antibody (green) binding is shown with Pearson's correlation coefficient ρ=0.50. High magnification image of dashed red and green boxes in A) show increased staining of KSP*-Cy5.5 peptide reagent (red) to E) dysplasia versus F) normal. High magnification image of dashed red and green boxes in B) show increased staining of anti-HER2-AF488 antibody (green) to G) dysplasia versus H) normal. I) From immunofluorescence, the mean (±sem) intensities were found to be 2.72±0.31, 0.12±0.08, 6.07±0.73, and 11.9±0.61 for normal (n=30), hyperplastic polyps (n=12), sessile serrated adenomas (n=13), and sporadic adenomas (n=30), respectively. The P-values for differences in the mean results for sporadic adenomas and that for normal, hyperplastic polyps, and sessile serrated adenomas were P=3.6×$10^{-5}$, P=8.7×$10^{-12}$, and P=0.03, respectively, by Tukey's multiple comparisons. The difference between the mean intensities for SSA and normal colon was P=0.20.

We demonstrate potential for clinical translation of the HER2 peptide reagent by examining specific binding to over expressed HER2 on formalin-fixed, paraffin-embedded (FFPE) specimens of human proximal colon. On confocal microscopy, we observed greater binding of both KSP*-Cy5.5 (red) and AF488-labeled anti-HER2 antibody (green) to dysplastic versus normal crypts on adjacent sections, FIG. 6A,B, respectively. Corresponding histology (H&E) is shown; FIG. 6C. At higher magnification, co-localization of peptide reagent and antibody binding to the surface (arrow) of dysplastic colonocytes can be seen, FIG. 6D. Also, differences in fluorescence intensities between dysplasia and normal from the dashed red and green boxes in FIG. 6A with KSP*-Cy5.5 (red) can be appreciated, FIG. 6E,F. Differences in fluorescence intensities between dysplasia and normal from the dashed red and green boxes in FIG. 6B with AF488-labeled anti-HER2 antibody (green) can be seen, FIG. 6G,H. Quantified fluorescence intensities (mean±std) for normal (n=30), hyperplastic polyps (n=12), sessile serrated adenomas (n=13), and sporadic adenomas (n=30) are shown, FIG. 6I. The mean result for adenoma was significantly greater than that for normal, hyperplasia, and SSA, while the difference between SSA and normal was not statistically significant.

Example 10

Overexpression of HER2 in Human Proximal Colon

Figures 6I, 6J:
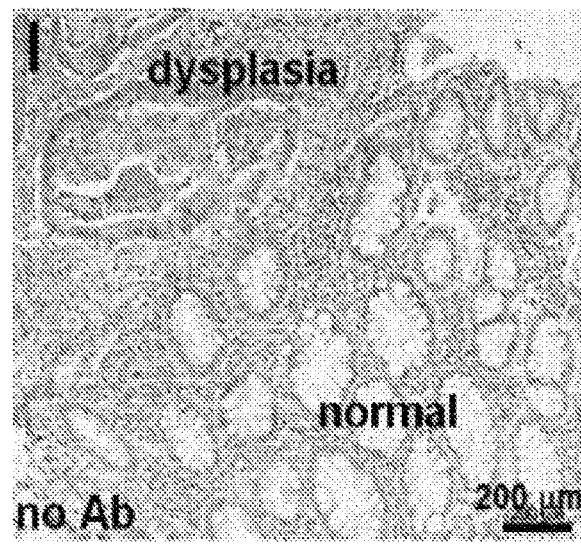

We performed immunohistochemistry with a known antibody to validate over expression of HER2 in human colonic dysplasia. We observed weak staining (0+/1+) of HER2 either on the membrane or in the cytoplasm of cells in the epithelium of normal colon and hyperplastic polyps, FIG. 7A,B. By comparison, we found various intensities of staining in dysplastic crypts for both sessile serrated adenomas (SSA) and sporadic adenomas, FIG. 6C,D. Contrast in reactivity between dysplasia and normal can appreciated for both polypoid and flat adenomas, FIG. 6E,G. Differences in HER2 expression between neoplasia and normal crypts in the same field-of-view support HER2 expression specific to dysplasia. Magnified views show intense staining on the membrane of dysplastic colonocytes, FIG. 6F,H. The control experiment was performed without use of primary antibody, FIG. 6I. An expert GI pathologist (SRO) using a standard IHC scoring system revealed overexpression, defined by either 2+ or 3+ staining, in 0% (0/30) of normal, 25% (3/12) of hyperplastic polyps, 14% (2/14) of SSA, and 41% (12/29) of adenomas, FIG. 6J. These results support HER2 as a promising early target for detection of proximal colon cancers.

Example 11

Discussion

We found KSP*-Cy5.5 to bind to HER2 with kd=21 nM. While antibodies can achieve much high binding affinities needed for therapeutic applications, this result is adequate for diagnostic imaging. This peptide reagent was found to bind rapidly with topical administration, k=0.14 min-1 (7.1 min). This feature is well suited to provide efficient surveillance in procedure units that perform endoscopic procedures in high volume. We found this peptide reagent to have no effect on HER2 signaling. For the diagnostic imaging, this property offers an advantage over other targeting moieties that are known to stimulate the HER2 signaling pathway and result in modulation of cell proliferation and tumorigenesis. We labeled the HER2 peptide with Cy5.5 because of its high quantum yield, photostability, and deep tissue penetration with NIR emission.4 This peptide may also be used to guide patient therapy by provide a more comprehensive picture of HER2 expression in tumors that are highly heterogeneous. The selection criteria for HER2 targeted therapy has previously depended mainly on IHC and FISH, which is evaluated on biopsy specimens obtained from only a small foci of diseased tissue.

We demonstrated specific peptide reagent binding to spontaneous colonic adenomas in mice that were either polypoid or flat in morphology during both in vivo and ex vivo validation using topical and systemic injection. The fluorescent signal from KSP*-Cy5.5 correlates with both polypoid and flat polyps and allows the detection of adenomas from surrounding non-neoplastic mucosa, suggesting that KSP*-Cy5.5 can be used as a tool for improving detection of colorectal adenomas using colonoscopy. It is possible that when the KSP*-Cy5.5 administered intravenously, the probe is more accessible than when administered locally, because of only partial penetration through the colonic mucosal layer. This might explain the improved TBR that we achieved when the probe was administered intravenously (FIG. 4C vs. 3G). Finally, we found significantly greater fluorescence intensity from peptide reagent binding to SSA and adenomas from human proximal colon compared to normal and hyperplastic polyps.

Example 12

Co-Localization of Peptide Reagent and Antibody on Human BilIN Specimens.

Formalin-fixed, paraffin-embedded (FFPE) specimens of human BilIN were obtained from an archived tissue bank. We used human BilIN specimens with various histological grades from n=22 patients, including n=7 with low grade (BilIN-1), n=4 with moderate grade (BilIN-2), n=5 with high grade (BilIN-3), and n=6 with carcinoma. We used adjacent normal biliary epithelium from the same specimen for control. Some of these normal specimens contained inflammation. 5 µm thick sections were cut, and mounted onto glass slides (Superfrost Plus, Fischer Scientific). The tissues were deparaffinized, and antigen retrieval was performed. The sections were blocked with protein serum for 15 min at room temperature followed by rinsing with PBS. The sections were then stained with KSP*-Cy5.5 at 5 µM concentration for 10 min at room temperature. The sections were then washed 3× with PBS (3 min each) and incubated overnight with anti-ErbB2 antibody (#2165, Cell Signaling Technology) at a dilution of 1:400. The sections were washed 3× with PBST, and incubated with (1:500) goat anti-rabbit antibody labeled with AF488 (Invitrogen) for 1 hour at room temperature. The sections were washed again 3× with PBST and mounted with Prolong Gold reagent containing DAPI (Invitrogen) using #1 cover glass (1.5 µm thickness). The images were collected with the same exposure time for all specimens.

Figures 10A, 10B, 10C, 10D, 10E, 10F:
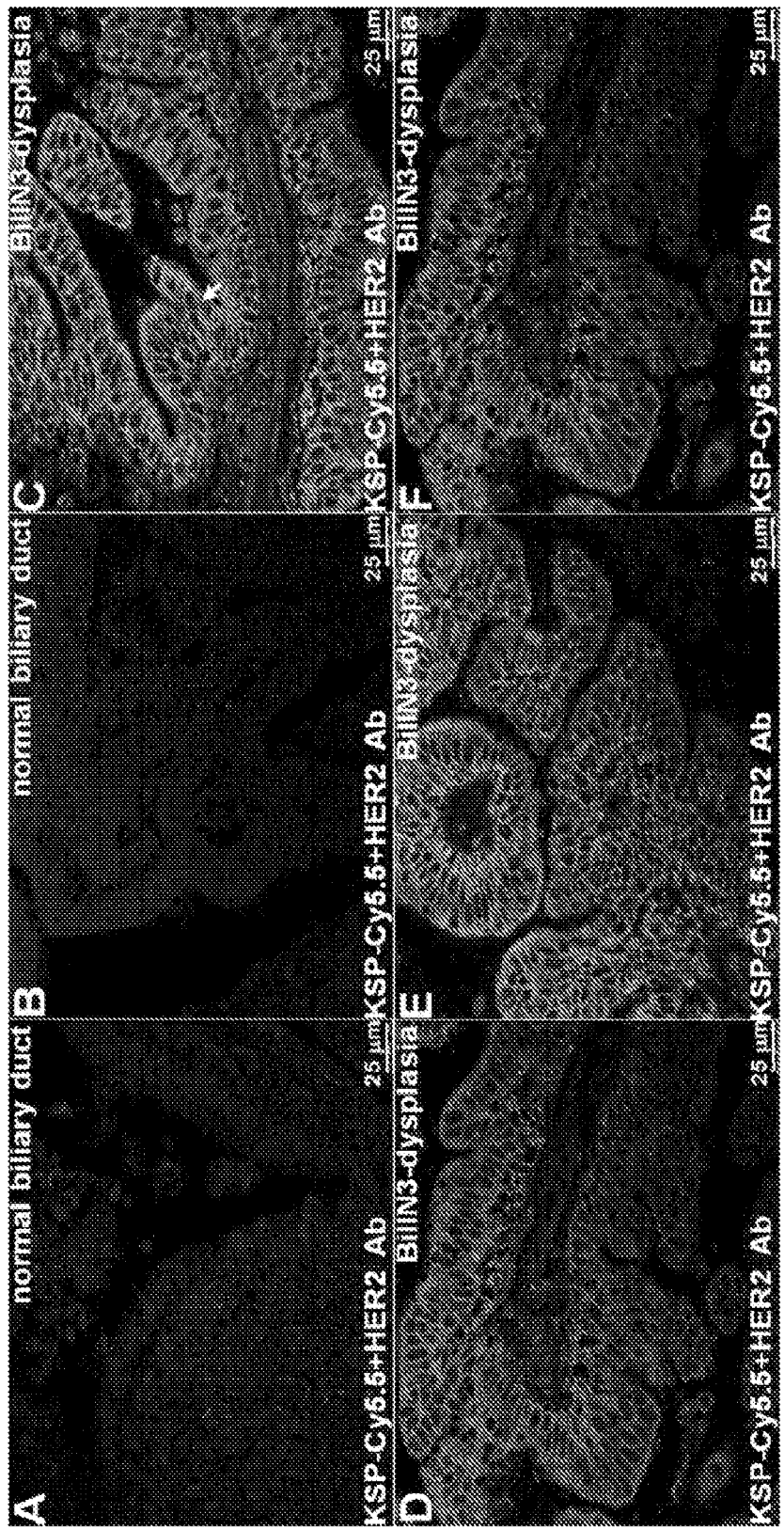
FIG. 10—Co-localization of peptide reagent and antibody on human BilIN specimens. A,B) Sections of normal human biliary duct show minimal staining with either the KSP*-Cy5.5 peptide reagent or the HER2 antibody. C-F) Sections of human BilIN show increased cell surface staining (arrows) with the KSP*-Cy5.5 peptide reagent that localizes with the HER2 antibody.

Sections of normal human biliary duct showed minimal staining with either the KSP*-Cy5.5 reagent or the HER2 antibody (FIG. 10A,B). Sections of human BilIN showed increased cell surface staining with the KSP*-Cy5.5 reagent that localizes with the HER2 antibody.

Example 13

Figure 11A:
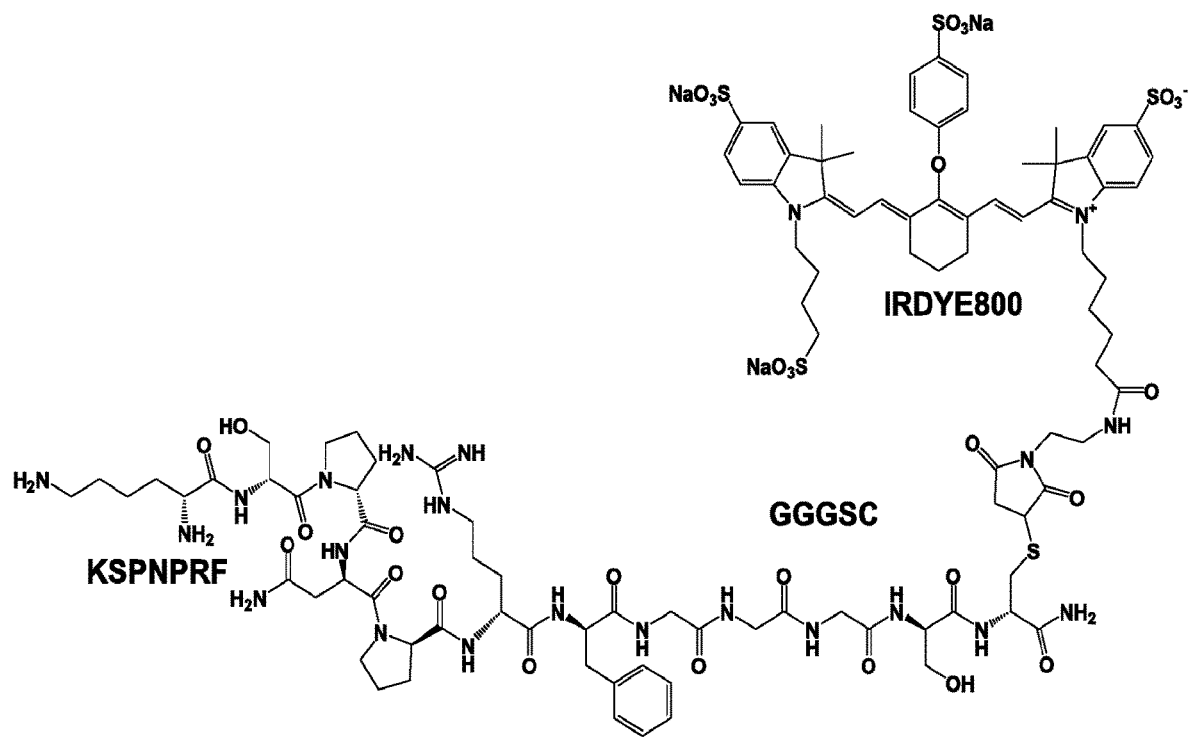
FIG. 11—Exemplary reagents comprising peptide reagents specific for HER2. A, B) Peptides labeled with near-infrared dye, such as IRDYE800, via a linker for use in imaging.
Figure 11B:
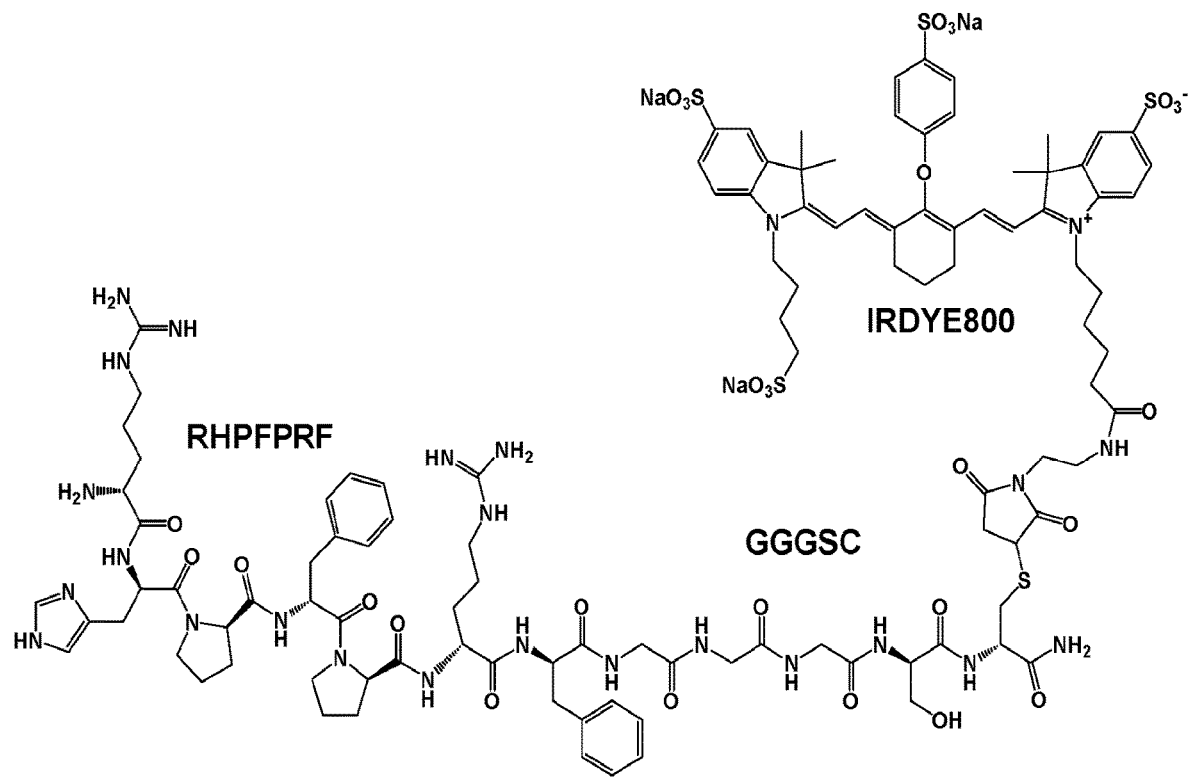

Peptides KSPNPRF (SEQ ID NO: 1) and RHPFPRF (SEQ ID NO: 2) were labeled with near-infrared dye via a linker GGGSC (SEQ ID NO: 7) for use in targeted detection with deep tissue imaging. The peptides were labeled with IRDYE800 using Maleimide chemistry in solution phase synthesis. See FIG. 11A,B.

Example 14

Specific Binding of Peptide Reagents to HER2 Overexpressed in Human Barrett's Esophagus Formalin-fixed, paraffin-embedded (FFPE) specimens of human esophagus were obtained from an archived tissue bank. 5 µm thick sections were cut, and mounted onto glass slides (Superfrost Plus, Fischer Scientific). The tissues were deparaffinized, and antigen retrieval was performed. The sections were blocked with protein serum for 15 min at room temperature followed by rinsing with PBS. The sections were then stained with either KSP*-Cy5.5 or RHP*-Cy5.5 at 5 µM concentration for 10 min at room temperature. The sections were then washed 3× for 3 min with PBS and further incubated with anti-HER2 antibody overnight at 4° C. Sections were washed 3× with PBST and mounted with Prolong Gold reagent containing DAPI (Invitrogen) using #1 cover glass (1.5 µm thickness).

FIG. 12A-E shows staining with KSP-Cy5.5 peptide reagent results in increasing fluorescence intensity upon in cancer progression in excised human Barrett's esophagus specimens. FIG. 12F-J shows minimal staining is observed with PPS*-Cy5.5, a scrambled peptide reagent used for control. Similarly, FIG. 13A-E shows staining with RHP*-Cy5.5 peptide reagent results in increasing fluorescence intensity with cancer progression in exised human Barrett's esophagus specimens, while FIG. 13F-J shows minimal staining is observed with PPF*-Cy5.5, a scrambled peptide reagent used for control.

While the present invention has been described in terms of specific aspects and embodiments, it is understood that variations and modifications will occur to those skilled in the art. Accordingly, only such limitations as appear in the claims should be placed on the invention.

All documents cited in this application are hereby incorporated by reference in their entirety, with particular attention to the disclosure for which they are referred.

We claim:

1. A reagent consisting essentially of a peptide KSPNPRF (SEQ ID NO: 1), RHPFPRF (SEQ ID NO: 2), RHPWPNR (SEQ ID NO: 3), RHPYPQR (SEQ ID NO: 4) or RKPFPRH (SEQ ID NO: 5), or a multimer form of the peptide,
wherein the peptide specifically binds to HER2 and
wherein at least one detectable label, at least one therapeutic moiety, or both, are attached to the peptide or a multimer form of the peptide.

2. The reagent of claim 1 comprising at least one detectable label attached to the peptide.

3. The reagent of claim 2 wherein the detectable label is detectable by microscopy, photoacoustic, ultrasound, positron emission tomography, single photon emission computed tomography or magnetic resonance imaging.

4. The reagent of claim 3 wherein the detectable label is fluorescein isothiocyanate (FITC).

5. The reagent of claim 3 wherein the detectable label is Cy5.

6. The reagent of claim 3 wherein the detectable label is Cy5.5.

7. The reagent of claim 3 wherein the detectable label is IRDYE800.

8. The reagent of claim 1 comprising at least one therapeutic moiety attached to the peptide.

9. The reagent of claim 8 wherein the therapeutic moiety is chemotherapeutic agent.

10. A composition comprising the reagent of claim 1 and a pharmaceutically acceptable excipient.

11. A method for detecting dysplasia in a patient comprising the steps of administering the reagent of claim 2 and detecting binding of the reagent to dysplastic cells.

12. A method for detecting early cancer in a patient comprising the steps of administering the reagent of claim 2 to the patient and detecting binding of the reagent to early cancer cells.

13. A method for detecting cancer in a patient comprising the steps of administering the reagent of claim 2 to the patient and detecting binding of the reagent to cancer cells.

14. A method of determining the effectiveness of a treatment for cancer and/or cancer metastasis, or recurrence of cancer in a patient comprising the step of administering the reagent of claim 2 to the patient, visualizing a first amount of cells labeled with the reagent, and comparing the first amount to a previously-visualized second amount of cells labeled with the reagent,
wherein a decrease in the first amount cells labeled relative to the previously-visualized second amount of cells labeled is indicative of effective treatment.

15. A method for delivering a therapeutic moiety to dysplastic cells of a patient comprising the step of administering the reagent of claim 8 to the patient.

16. A method for delivering a therapeutic moiety to early cancer cells of a patient comprising the step of administering the reagent of claim 8 to the patient.

17. A method for delivering a therapeutic moiety to cancer cells of a patient comprising the step of administering the reagent of claim 8 to the patient.

18. A kit for administering the composition of claim 10 to a patient in need thereof, said kit comprising the composition of claim 10 and instructions for use of the composition.

19. A peptide consisting of the amino acid sequence KSPNPRF (SEQ ID NO: 1), RHPFPRF (SEQ ID NO: 2), RHPWPNR (SEQ ID NO: 3), RHPYPQR (SEQ ID NO: 4) or RKPFPRH (SEQ ID NO: 5).

20. The kit of claim 18 further comprising an endoscope for administering the composition to a patient.

* * * * *

SEQUENCE LISTING

```
<160> NUMBER OF SEQ ID NOS: 8

<210> SEQ ID NO 1
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1

Lys Ser Pro Asn Pro Arg Phe
1               5

<210> SEQ ID NO 2
<211> LENGTH: 7
```

```
<212> TYPE: PRT
<213> ORGANISM: Artificial Sequence
<220> FEATURE:
<223> OTHER INFORMATION: Synthetic peptide

<400> SEQUENCE: 2

Arg His Pro Phe Pro Arg Phe
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic peptide

<400> SEQUENCE: 3

Arg His Pro Trp Pro Asn Arg
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic peptide

<400> SEQUENCE: 4

Arg His Pro Tyr Pro Gln Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic peptide

<400> SEQUENCE: 5

Arg Lys Pro Phe Pro Arg His
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic peptide

<400> SEQUENCE: 6

Gly Gly Gly Ser Lys
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic peptide

<400> SEQUENCE: 7

Gly Gly Gly Ser Cys
1               5

<210> SEQ ID NO 8
<211> LENGTH: 7
<212> TYPE: PRT
```

```
<213> ORGANISM: Artificial Sequence
<220> FEATURE:
<223> OTHER INFORMATION: Synthetic peptide

<400> SEQUENCE: 8

Pro Pro Ser Asn Phe Lys Arg
1               5
```